US011007228B2

(12) United States Patent
Bae et al.

(10) Patent No.: US 11,007,228 B2
(45) Date of Patent: May 18, 2021

(54) PHARMACEUTICAL COMPOSITION CONTAINING STEM CELL IN WHICH VASCULAR ENDOTHELIAL GROWTH FACTOR IS OVEREXPRESSED AS EFFECTIVE INGREDIENT FOR PREVENTING OR TREATING NEURODEGENERATIVE DISEASE

(71) Applicant: Kyungpook National University Industry-Academic Cooperation Foundation, Daegu (KR)

(72) Inventors: Jae Sung Bae, Daegu (KR); Hee Kyung Jin, Daegu (KR); Min Hee Park, Gyeongsangbuk-do (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 188 days.

(21) Appl. No.: 16/075,517

(22) PCT Filed: Feb. 3, 2017

(86) PCT No.: PCT/KR2017/001216
§ 371 (c)(1),
(2) Date: Aug. 3, 2018

(87) PCT Pub. No.: WO2017/135753
PCT Pub. Date: Aug. 10, 2017

(65) Prior Publication Data
US 2019/0030082 A1    Jan. 31, 2019

(30) Foreign Application Priority Data

Feb. 5, 2016    (KR) .......................... 10-2016-0015093

(51) Int. Cl.
A61K 35/30 (2015.01)
A61K 9/00 (2006.01)
A61K 35/28 (2015.01)
A61K 35/12 (2015.01)
A61K 35/545 (2015.01)
A61P 25/28 (2006.01)
C07K 14/49 (2006.01)

(52) U.S. Cl.
CPC ............... *A61K 35/30* (2013.01); *A61K 9/00* (2013.01); *A61K 9/0085* (2013.01); *A61K 35/12* (2013.01); *A61K 35/28* (2013.01); *A61K 35/545* (2013.01); *A61P 25/28* (2018.01); *C07K 14/49* (2013.01)

(58) Field of Classification Search
CPC ........ A61K 35/30; A61K 9/0085; A61K 9/00; A61K 35/28; A61K 35/12; A61K 35/545; A61K 9/0019; A61P 25/28; C07K 14/49
USPC ..................................................... 424/93.21
See application file for complete search history.

(56) References Cited

U.S. PATENT DOCUMENTS 9,724,334 B1    8/2017 Bae et al.
2006/0141622 A1*   6/2006 Johe ........................ A61P 25/14
                                                              435/368

FOREIGN PATENT DOCUMENTS

KR    10-2009-0008155 A    1/2009
KR       10-1293424 B1    8/2013
KR    10-2015-0122043 A   10/2015
KR    10-2016-0008987 A    1/2016

OTHER PUBLICATIONS

Jingiao Sun et al., Biochemical and Biophysical Research Communications, 2010, 394: 146-152 (Year: 2010).*
Jinqiao Sun et al., Biochemical and Biophysical Research Communications, 2010, 394: 146-152 (Year: 2010).*
Hyun Lee et al., Nature Communications, Nov. 24, 2014, 5: 5514 (Year: 2014).*
Josephine Herz et al., Neurobiology of Disease, 2012, 45: 1077-1085 (Year: 2012).*
Xiong et al., "VEGF-expressing human umbilical cord mesenchymal stem cells, an improved therapy strategy for Parkinson's disease"; Gene Therapy, 18: 394-402; Nov. 25, 2010). (Year: 2010).*
International Search Report corresponding to Korean Patent Application Serial No. PCT/KR2017/001216 dated Apr. 26, 2017.
Xiong et al., "VEGF-expressing human umbilical cord mesenchymal stem cells, an improved therapy strategy for Parkinson's disease," Gene Therapy, vol. 18, pp. 394-402 (2011).
Angevine et al., "Autoradiographic Study of Cell Migration during histogenesis of Cerebral Cortex in the Mouse," Nature, vol. 192, pp. 766-768 (1961).
Caviness et al., "Proliferative events in the cerebral ventricular zone," Brain & Development, vol. 17, pp. 159-163 (1995).
Chaves et al., "Sphingolipids and gangliosides of the nervous system in membrane function and dysfunction," FEBS Letters, vol. 584, pp. 1748-1759 (2010).
Curtis et al., "The effect of neurodegenerative diseases on the subventricular zone," Nature Reviews Neuroscience, vol. 8, pp. 712-723 (2007).

(Continued)

*Primary Examiner* — Scott Long
(74) *Attorney, Agent, or Firm* — Jenkins, Wilson, Taylor & Hunt, P.A.

(57) ABSTRACT

The present invention relates to a pharmaceutical composition containing stem cells in which vascular endothelial growth factor (VEGF) is overexpressed as an effective ingredient for preventing or treating neurodegenerative diseases. The stem cells in which VEGF is overexpressed according to the present invention effectively act against the neurodegenerative disease-induced VEGF reduction of neural stem cells in the SVC to inhibit the abnormal migration of neural stem cells, suppress inflammatory responses, and restrain the accumulation of cholesterol and spingolipids in the cerebral cortex, thus restoring the behavior exercise capacity of animal models, whereby the pharmaceutical composition can be used as an effective therapeutic agent for neurodegenerative diseases.

5 Claims, 17 Drawing Sheets

(56) References Cited

OTHER PUBLICATIONS

Dehay et al., "Cell-cycle control and cortical development," Nature Reviews Neuroscience, vol. 8, pp. 438-450 (2007).
GenBank ID: NM_001025366.2, "*Homo sapiens* vascular endothelial growth factor A (VEGFA), transcript variant 1, Mrna," accessed Sep. 26, 2018.
Horgusluoglu et al., "Adult Neurogenesis and Neurodegenerative Diseases: A Systems Biology Perspective," Am J Med Genet B Neuropsychiatr Genet., vol. 174, No. 1, pp. 93-112 (2017). [Author manuscript, pp. 1-38].
Mani et al., "Vascular Endothelial Growth Factor Enhances Migration of Astroglial Cells in Subventricular Zone Neurosphere Cultures," Journal of Neuroscience Research, vol. 88, pp. 248-257 (2010).
Ming et al., "Adult Neurogenesis in the Mammalian Brain: Significant Answers and Significant Questions," Neuron, vol. 70, pp. 687-702 (2011).
Molyneaux et al., "Neuronal subtype specification in the cerebral cortex," Nature Reviews Neuroscience, vol. 8, pp. 427-437 (2007).
Platt et al., "Sphingolipid lysosomal storage disorders," Nature, vol. 510, pp. 68-75 (2014).
Sillence et al., "Storage diseases: new insights into sphingolipid functions," Trends in Cell Biology, vol. 13, No. 4, pp. 195-203 (2003).
Wittko et al., "VEGFR-1 Regulates Adult Olfactory Bulb Neurogenesis and Migration of Neural Progenitors in the Rostral Migratory Stream In Vivo," Journal of Neuroscience, vol. 29, No. 27, pp. 8704-8714 (2009).
Shibuya (1995) "Role of VEGF-Flt Receptor System in Normal and Tumor Angiogenesis," Advances in Cancer Research, vol. 67, pp. 281-316.

\* cited by examiner

■ GFAP/CD133 cre;+/+
☰ GFAP/CD133 cre;NPC1$^{fl/fl}$
▨ GFAP/CD133 cre;VEGF$^{fl/fl}$ ■ GFAP/CD133 cre;+/+
☰ GFAP/CD133 cre;NPC1$^{fl/fl}$
▨ GFAP/CD133 cre;VEGF$^{fl/fl}$

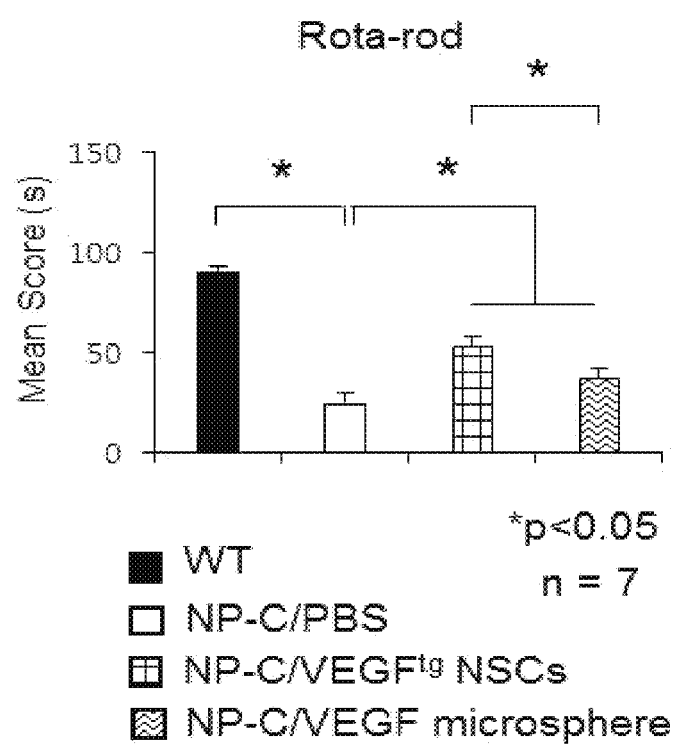

PHARMACEUTICAL COMPOSITION CONTAINING STEM CELL IN WHICH VASCULAR ENDOTHELIAL GROWTH FACTOR IS OVEREXPRESSED AS EFFECTIVE INGREDIENT FOR PREVENTING OR TREATING NEURODEGENERATIVE DISEASE

TECHNICAL FIELD

The present application claims priority from Korean Patent Application No. 10-2016-0015093, filed on Feb. 5, 2016, the entire contents of which are incorporated herein by reference.

The present invention relates to a pharmaceutical composition for preventing or treating a neurodegenerative diseases comprising stem cells overexpressing vascular endothelial growth factor (VEGF) as an active ingredient.

BACKGROUND OF THE INVENTION

With the global increase in an aging population, the morbidity of neurodegenerative diseases (NDDs) is expected to overtake that of cancer, which is the second cause of death after cardiovascular diseases. Accordingly, the market for therapies for neurodegenerative diseases has also highly grown by about 20% every year since 2000. As such, the interest in neurodegenerative diseases is increasing day by day.

Neurodegenerative diseases lead to death by causing loss of cognitive ability and loss of motor functions resulting from gradual neural apoptosis. Niemann-pick disease, Alzheimer's disease (AD), Parkinson's disease (PD), and the like, are representative of neurological diseases, of which the frequency increases according to aging. The correlation between brain aging and neurodegenerative diseases is not yet completely revealed so far, but the brain aging and the neurodegenerative diseases have many overlapping characteristics, such as apoptosis of brain cells and a reduction in brain volume.

Of these neurodegenerative diseases, Niemann-Pick disease is a rare autosomal recessive hereditary disease showing various clinical symptoms by cholesterol and glycolipid accumulation in several organs due to metabolic disorders of sphingolipids. Niemann-Pick diseases are classified into types A, B, C, and D according to the causative gene and clinical aspect, and types A and B were first found to be caused by deficiency of sphingomyelinase, and thereafter, types C and D were found to be caused by transport disorder of cholesterol. Type C, which shows clinically sub-acute, various chronic progresses, is known to show a prevalence of about 0.6-0.8 per 100,000 persons according to a report, and type C1 by the mutation of NPC1 gene accounts for about 95% of the overall cases. Niemann-Pick type C disease shows a pattern in which cholesterol is characteristically accumulated in internal organs and nerve systems, and a symptom is expressed according to the organ in which cholesterol is accumulated and the fatality rate is mainly determined depending on the progress of central nervous system deposition. According to recent studies, sphingosine is a main deposition material in Niemann-Pick type C disease. Niemann-Pick type C disease may have clinically various progresses, and the time of onset is reported to be various from newborn babies to the seventies, and the disease period is from a few days to 60 years. Hepatosplenomegaly, gait disturbance, ocular motor dysfunction, and cognitive disorder are comparatively distinctively observed.

The disease selectively well invades the cerebellum and brain stem in the central nervous system, causing demyelination and the degeneration of cerebellar Purkinje cells, and thus inducing related symptoms. However, there is no adequate medicine for this disease so far, and thus the development of a preventive and therapeutic agent for Niemann-Pick disease is urgently needed.

Meanwhile, vascular endothelial growth factor (VEGF) is one of the most important growth factors involved in angiogenesis. VEGF stimulates endothelial cells through PKC, and then induces ERK1/2 activation, but the accurate mechanisms thereof have not been known. In addition, the VEGF receptors are found in various cancer tissues, and the cell division stimulating effect of VEGF in cancer cells has been reported. Recently, there is an increasing trend in reports of correlations between VEGF and neurodegenerative diseases.

In addition, the present inventors have also confirmed in conventional studies and patents (KR Patent Application 10-2014-0149347) that the administration of VEGF can be used in the treatment and prevention of Niemann-Pick diseases, but studies about appropriate delivery and administration of VEGF have not yet been reported.

DETAILED DESCRIPTION OF THE INVENTION

Technical Problem

The present inventors endeavored to specify effective delivery and administration sites of vascular endothelial growth factor (VEGF), and as a result, confirmed that when stem cells overexpressing vascular endothelial growth factor are directly injected into the subventricular zone (SVZ) of Niemann-Pick disease animal models, VEGF is effectively delivered to SVZ with reduced VEGF, and then the present inventors completed the present invention.

Accordingly, an aspect of the present invention is to provide a pharmaceutical composition for preventing or treating of neurodegenerative diseases comprising stem cells overexpressing vascular endothelial growth factor (VEGF) as an active ingredient.

Another aspect of the present invention is to provide use of stem cells overexpressing vascular endothelial growth factor (VEGF) for preparing an agent for the prevention or treatment of a neurodegenerative disease.

Still another aspect of the present invention is to provide a method for preventing or treating a neurodegenerative disease in a subject, the method comprising administering an effective amount of stem cells overexpressing vascular endothelial growth factor (VEGF) to a subventricular zone (SVZ) of a subject in need thereof.

Technical Solution

An embodiment according to an aspect of the present invention provides a pharmaceutical composition for preventing or treating of neurodegenerative diseases comprising stem cells overexpressing vascular endothelial growth factor (VEGF) as an active ingredient.

An embodiment according to another aspect of the present invention provides use of stem cells overexpressing vascular endothelial growth factor (VEGF) for preparing an agent for the prevention or treatment of a neurodegenerative disease.

An embodiment according to still another aspect of the present invention provides a method for preventing or treating a neurodegenerative disease in a subject, the method comprising administering an effective amount of stem cells overexpressing vascular endothelial growth factor (VEGF) to a subventricular zone (SVZ) of a subject in need thereof.

Hereinafter, the present invention will be described in detail.

The present invention provides a pharmaceutical composition for preventing or treating of neurodegenerative diseases comprising stem cells overexpressing vascular endothelial growth factor (VEGF) as an active ingredient.

As used herein, the term "vascular endothelial growth factor (VEGF)" refers to a growth factor selectively acting on vascular endothelial cells and is composed of 34-42 kDa glycoprotein, and it is known that VEGF acts on VEGFR-1 as a receptor on the cell membrane, thereby activating phospholipase C to increase vascular endothelial cells, increasing the vascular permeability to release plasma proteins, and depositing celluloses to induce angiogenesis (See Shibuya, 1995).

The nucleotide sequence coding the vascular endothelial growth factor (VEGF) is the nucleotide sequence of GenBank ID: NM_001025366.2.

The vascular endothelial growth factor (VEGF) includes proteins having an amino acid sequence coded by the nucleotide sequence and functional equivalents of the proteins. "Functional equivalents" refer to a protein exhibiting substantially the same activity as VEGF encoded by the sequence, having at least 70%, preferably at least 80%, more preferably at least 90%, and most preferably at least 95% sequence homology with the sequence, as a result of addition, substitution or deletion of amino acids.

As used herein, the term "stem cells" refers to undifferentiated cells that have the potency to differentiate into various body tissues, and may be classified into totipotent stem cells, pluripotent stem cells, and multipotent stem cells.

In the present invention, the stem cells may be adult stem cells, embryonic stem cells, mesenchymal stem cells, tumor stem cells, or induced pluripotent stem cells.

In addition, the adult stem cells may be neural stem cells or neural progenitor cells. Neural stem cells (NSCs) are cells that enable self-renewal and has the potency to differentiate into nervous system cells, and the neural stem cells may differentiate into neurons, astrocytes, oligodendrocytes.

As used herein, the term "mesenchymal stem cells (MSCs)" are multipotent stem cells that have the potency to differentiate into several mesoblastic cells including bone, cartilage, fat, and muscle cells or also ectodermal cells, such as neurons. The mesenchymal stem cells may preferably originate from the group consisting of umbilical cord, umbilical cord blood, bone marrow, fat, muscle, nerve, skin, amniotic membrane, chorionic membrane, decidual membrane, and placenta. In addition, the mesenchymal stem cells may originate from humans, fetus, or mammals other than humans. The mammals other than humans are more preferably the dog family animals, the cat family animals, the monkey family animals, cattle, sheep, pig, horse, rat, mouse, guinea pig, or the like, and the origins thereof are not limited.

The active ingredient has a concept encompassing a stem cell culture containing the stem cells, a concentrate of the culture, and the like.

The vascular endothelial growth factor (VEGF)-overexpressed stem cells of the present invention may be obtained by a recombinant vector including the gene coding vascular endothelial growth factor. The recombinant vector needs to overexpress VEGF gene in stem cells, and thus is preferably in a form of a recombinant expression vector. The recombinant expression vector may be prepared by operatively linking APP coding nucleic acid and a control signal (e.g., promoter, secretory sequence, enhancer, upstream activation sequence, transcription termination factor, or the like) capable of exerting functions in canine nervous system cells, to a base vector (i.e., backbone vector) that is commercially available. The recombinant expression vector may include a selective marker, and the selective marker includes antibiotic agent resistance genes, such as kanamycin resistance gene and neomycin resistance gene, and fluorescent proteins, such as green fluorescent protein and red fluorescent protein, but is not limited thereto.

The transformation may be carried out by known methods, including, for example, calcium phosphate transfection, electrophoresis, transduction, DEAE-dextran mediated transfection, microinjection, cationic lipid-transfection, ballistic introduction, and the like, but are not limited thereto.

Especially, the pharmaceutical composition for prevention or treatment of the neurodegenerative diseases of the present invention is characterized by being directly injected into the subventricular zone (SVZ) of a subject.

A neural plate becomes a neural tube during early development, and a cavity within the neural tube forms a ventricle through the developmental process. The cell layer closest to the ventricle is the ventricular zone. An additional proliferating cell layer is formed above the ventricular zone through a neurogenesis process, which is referred to as the subventricular zone. The progenitor cells in the ventricular zone and the subventricular zone have properties of neural stem cells, and can differentiate into neurons, astrocytes, and oligodendrocytes, which constitute the nervous system, through complex control methods (See Dehay and Kennedy, Nat RevNeurosci 8:438-450, 2007; Molyneaux et al., NatRevNeurosci 8:427-437, 2007; Angevine and Sidman, Nature 192:766-768, 1961; Caviness and Takahashi, BrainDev17:159-163, 1995).

The neural stem cells in the normal SVZ environments migrate into the olfactory bulb (OB) through rostral migratory stream (RMS) to differentiate into neurons. Various signaling systems control the migration pattern of these neural stem cells, and according to conventional reports, VEGF is one of such control signals (Neuron. 70, 687-702 (2011), J Neurosci. 29, 8704-8714 (2009), J Neurosci Res. 88, 248-257 (2010).)

According to an example of the present invention, it was confirmed that neural stem cells existing in SVZ of Niemann-Pick disease mice had a significantly reduced expression of VEGF compared with normal mice, and these neural stem cells showed an abnormal aspect of migrating to the thalamus but not the normal migration path. Resultingly, Niemann-Pick disease mice had increased inflammation responses in the thalamus and cortex thereof and accumulated cholesterol and sphingolipids in the brain thereof, resulting in the impairment of animal sensory functions and motor functions.

Meanwhile, the present inventors directly administered VEGF-overexpressed neural stem cells into the SVZ of Niemann-Pick disease mice, and as a result, abnormal migration of neural stem cells were reduced, the inflammation responses were suppressed in the thalamus and cortex, the animal sensory functions and motor functions were restored, and even the survival rate was improved.

The present inventors administered SVZ of Niemann-Pick disease mice with normal neural stem cells or a vector capable of overexpressing VEGF, besides VEGF-overexpressed neural stem cells, and as a result, no improvement was observed. That is, it was confirmed that the damaged SVZ environment could not be improved by only any one of normal neural stem cells and VEGF, and such an effect can be exerted only when administration was carried out in a form of VEGF-overexpressed neural stem cells.

It has not been reported so far that the damage to SVZ plays a fundamental role in the onset of Niemann-Pick disease and the improvement of SVZ environment can prevent or treat various neurodegenerative diseases including Niemann-Pick disease, and thus these are first revealed through the present invention by the present inventors.

The term "damaged SVZ environment" refers to an abnormal migration aspect of neural stem cells existing in SVZ to the thalamus due to a reduction in VEGF expression, and the term "improvement" refers to suppressing abnormal migration of neural stem cells and restoring normal brain functions by administering VEGF-overexpressing neural stem cells into SVZ.

According to another example of the present invention, it was confirmed that when the SVZ environment was damaged, the survival rates of neural stem cells existing in the SVZ environment were decreased and sphingolipids and cholesterol were accumulated in the cerebral cortex. Meanwhile, the VEGF-overexpressed neural stem cells were directly administered into the damaged SVZ environment, and as a result, the survival rates of neural stem cells were increased and the accumulation of sphingolipids and cholesterol was reduced.

Therefore, the pharmaceutical composition of the present invention can exhibit an effect of preventing or treating Niemann-Pick disease, as well as neurodegenerative diseases caused by reduced neural stem cells in the SVZ environment and cholesterols or sphingolipids accumulation in the brain.

In the present invention, the neurodegenerative disease is selected from the group consisting of Niemann-Pick disease, Alzheimer's disease, Parkinson's disease, Lou Gehrig's disease, schizophrenia, Gaucher disease, Fabry disease, Tay-Sachs disease, Sandhoff disease and cerebellar ataxia. Preferably Niemann-Pick disease or cerebellar ataxia, most preferably Niemann-Pick disease, but is not limited thereto.

In the present invention, the Niemann-Pick disease is a disease caused by accumulation of lipids in reticuloendothelial cells, and corresponds to a hereditary disease. The Niemann-Pick disease of the present invention is not limited to the type thereof, and may be, for example, Niemann-Pick disease type A, B, C, D, E, or F disease.

Especially, the Niemann-Pick disease of the present invention may be Niemann-Pick type C disease. Niemann-Pick type C disease is a hereditary disease causing various kinds of nerve disorders, such as memory and intelligence disorders, resulting from the accumulation of sphingolipids and cholesterol in cells due to metabolic disorders of lipids, which are main organic materials constituting living bodies along with proteins and sugars.

According to an example of the present invention, the damage of SVZ environment resulted in a damage to cerebellar neurons, and thus the number of cerebellar neurons was decreased and the inflammation responses were increased, but as a result of administering VEGF-overexpressed neural stem cells into SVZ, the damage of cerebellar neurons was prevented and the inflammation responses were mitigated. Therefore, the administration of VEGF-overexpressed neural stem cells into SVZ can prevent or treat cerebellar ataxia.

In the present invention, the cerebellar ataxia refers to a neural disease in which motions are clumsy and the motions are not coordinated with each other due to cerebellar dysfunction, and includes all types of cerebellar ataxia caused by various medical and neurological diseases and genetic predispositions.

Alzheimer's disease, Parkinson's disease, Lou Gehrig's disease, and asthma, like Niemann-Pick disease, are diseases that have been reported to show a decreased number and proliferation of neural stem cells existing in the SVZ environment (See Nat Rev Neurosci. 2007 September; 8(9):712-23. Am J Med Genet B Neuropsychiatr Genet. 2017 January; 174(1):93-112). According to an example of the present invention, the administration of VEGF-overexpressed neural stem cells into SVZ resulted in increased survival rates of neural stem cells in the SVZ environment and decreased inflammation responses in the brain, and thus the neurodegenerative diseases can be prevented or treated by using the pharmaceutical composition of the present invention.

Meanwhile, Gaucher's disease, Fabry's disease, Tay-Sachs disease, and Sandhoff's disease are diseases that have been reported to be caused by the accumulation of lipids in the brain due to the disorder of lipid metabolism, like Niemann-Pick disease (See Nature. 2014 Jun. 5; 510(7503): 68-75, Trends Cell Biol. 2003 April; 13(4):195-203., FEBS Lett. 2010 May 3; 584(9):1748-59). According to an example of the present invention, the administration of VEGF-overexpressed neural stem cells into SVZ resulted in decreased accumulation of cholesterol and sphingolipids in the brain, and thus the neurodegenerative diseases can be prevented or treated by using the pharmaceutical composition of the present invention.

In the present invention, the pharmaceutical composition may comprise a pharmaceutically acceptable carrier Examples of the pharmaceutically acceptable carrier contained in the pharmaceutical composition of the present invention are those conventionally used in formulation and include, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include a lubricant, a humectant, a sweetener, a flavoring agent, an emulsifier, a suspending agent, and a preservative.

In addition, the composition of the present invention may be used in a form of a general medicinal preparation. A parenteral preparation may be prepared in a form of a sterile aqueous solution, a non-aqueous solvent, a suspending agent, oil, or a freeze-drying preparation. For oral administration, the composition of the present invention may be prepared in a form of a tablet, troche, capsule, elixir, suspension, syrup, or wafer. For injections, the composition may be prepared into a single-dose ampoule or multi-dose container. In addition, the composition for treatment of the present invention may be administered together with a pharmaceutically acceptable carrier.

For example, for oral administration, a binder, a lubricant, a disintegrator, an excipient, a solubilizer, a dispersing agent, a stabilizer, a suspending agent, a coloring agent, a perfume, or the like may be used. For injections, a buffer, a preservative, an analgesic, a solubilizer, an isotonic agent, a stabilizer, or the like may be used. For topical administration, a base, an excipient, a lubricant, a preservative, or the like may be used.

In addition, a method for treating neurodegenerative diseases by using the composition of the present invention may include administering to a patient through a general route in which a predetermined material is introduced in a proper manner. The manner of administration may be intraperitoneal, intravenous, intramuscular, subcutaneous, intradermal, oral, topical, intranasal, intrapulmonary, and intrarectal administration, but is not limited thereto. Most preferably, the manner of administration is a direct administration into the subventricular zone.

The pharmaceutical composition may be administered by any device that can deliver an active material to a target cell. Preferred manner of administration and preparations are intravenous, subcutaneous, intradermal, intramuscular, or drip injections. An injection may be prepared by using an aqueous solvent, such as physiological saline solution or Ringer's solution, and a non-aqueous solvent, such as vegetable oil, a higher fatty acid ester (for example, ethyl oleate), an alcohol (for example, ethanol, benzyl alcohol, propylene glycol or glycerin). The injection may contain a pharmaceutical carrier, such as a stabilizer for deterioration prevention (for example, ascorbic acid, sodium hydrogen sulfite, sodium pyrolactosulfate, BHA, tocopherol, EDTA, or the like), an emulsifier, a buffer for pH adjustment, a preservative for inhibiting microbial growth (for example, phenylmercuric nitrate, thimerosal, benzalkonium chloride, phenol, cresol, benzyl alcohol, or the like). The method for treating or preventing neurodegenerative diseases by using the composition of the present invention includes administering a pharmaceutical effective amount of the composition for treatment of the present invention. The pharmaceutical effective amount may be easily determined by a person skilled in the art according to factors well known in the art, including the kind of disease, age, body weight, health status, sex of a patient, drug sensitivity of a patient, route of administration, method of administration, number of times of administration, period of treatment, mixing, drug(s) used in combination.

The present invention can also provide a food composition containing vascular endothelial growth factor (VEGF)-overexpressed stem cells. The food composition may be a health functional food. The term "health functional food" refers to food having a biological modulation functions, such as prevention and alleviation of diseases, bio-defense, immunity, recovery after diseases, suppression of aging, or the like. The health functional food needs to be harmless to the human body when taken for a long period of time.

The active ingredient of the present invention may be added to a health functional food for the purpose of prevention or alleviation of neurodegenerative diseases. When the vascular endothelial growth factor (VEGF)-overexpressed stem cells of the present invention is used as a food additive, the vascular endothelial growth factor (VEGF)-overexpressed stem cells may be added per se, or may be used together with another food or food ingredient, and may be properly used according to a conventional method. The amount of an active ingredient mixed may be properly determined according to the purpose of use (prevention, health, or therapeutic treatment). The active ingredient of the present invention is generally added at an amount of 15 wt % or less, preferably 10 wt % or less, relative to the raw materials when food or drink is prepared. However, when the active ingredient is taken for a long period of time for the purpose of health and sanitation or health control, the amount of the active ingredient may be below the above range. Since the active ingredient is not problematic in view of safety, the active ingredient may be used at an amount above the above range.

There is no particular limitation on the kind of the food. Examples of the food to which the above substance can be added include meat, sausage, bread, chocolate, candies, snacks, cookies, pizza, ramen, other noodles, gums, dairy products including ice cream, various soups, beverages, teas, drinks, alcoholic beverages, vitamin complexes, and the like, and encompasses all types of health foods in an acceptable meaning.

The health drink composition of the present invention may contain various flavorants or natural carbohydrates as additional ingredients, like in ordinary drinks. The foregoing natural carbohydrates may include monosaccharides, such as glucose and fructose, disaccharides, such as maltose and sucrose, natural sweeteners, such as dextrin and cyclodextrin, and synthetic sweeteners, such as saccharin and aspartame. The proportion of the natural carbohydrate is generally about 0.01-10 g, and preferably about 0.01-0.1 g per 100 mL of the composition of the present invention.

In addition to above, the composition of the present invention may contain various nutrients, vitamins, electrolytes, flavorants, colorants, pectic acid and salts thereof, alginic acid and salts thereof, organic acids, protective colloid thickeners, pH adjusters, stabilizers, stabilizing agents, preservatives, glycerins, alcohols, carbonating agents used in carbonated drinks, and the like. In addition, the composition of the present invention may contain fruit flesh for manufacturing natural fruit juice, fruit juice drink, and vegetable drink. These ingredients may be used independently or in mixture. The proportion of such an additive is not greatly important, but is generally selected within a range of 0.01-0.1 parts by weight relative to 100 parts by weight of the composition of the present invention.

The term "treatment" of the present invention refers collectively to alleviate a degenerative neurological disease or symptoms of a degenerative neurological disease, may encompass curing, substantially preventing, or improving the condition of such a disease, and may include alleviating, curing, or preventing one or most of symptoms resulting from a degenerative neurological disease, but is not limited thereto.

In addition, the present invention provides use of stem cells overexpressing vascular endothelial growth factor (VEGF) for preventing of treating a neurodegenerative disease.

In addition, the present invention provides use of stem cells overexpressing vascular endothelial growth factor (VEGF) for preparing an agent for preventing or treating of a neurodegenerative disease which is to be administered to a subventricular zone (SVZ) of a subject.

In addition, the present invention provides a method for preventing or treating a neurodegenerative disease in a subject, the method comprising administering an effective amount of stem cells overexpressing vascular endothelial growth factor (VEGF) to a subventricular zone (SVZ) of a subject in need thereof.

As used herein, the term "effective amount" refers collectively to an amount by which, upon being administered to a subject, resulting in the inhibition of abnormal migration of neural stem cells into thalamus or the accumulation of cholesterols or sphingolipids in the cerebral cortex, the alleviation of inflammation in the cerebral cortex, or the recovery of the motor or sensory function of a subject. The term "subject" may be an animal, preferably a mammal, and especially, an animal including a human being, and may be a cell, a tissue, an organ, or the like, derived from an animal. The subject may be a patient in need of treatment.

The neurodegenerative disease is as described above.

Advantageous Effect

The vascular endothelial growth factor (VEGF)-overexpressed stem cells according to the present invention effectively restore the reduction of VEGF in neural stem cells in SVZ, which occurs by a neurodegenerative disease, thereby inhibiting abnormal migration of neural stem cells, suppressing inflammation responses, and suppressing the accumulation of cholesterol in the cerebral cortex, and thus inducing the restoration of behavior and motor abilities of animal models. Therefore, the VEGF-overexpressed stem cells according to the present invention can be utilized as an effective medicine for a neurodegenerative disease.

BRIEF DESCRIPTION OF THE DRAWINGS

FIGS. 8B to 8D confirm the inflammation responses (FIG. 8B), lipid accumulation (FIG. 8C), and the presence or absence of the improvement of motor function (FIG. 8D) after SVZ of NP-C mice was injected with VEGF-overexpressing neural stem cells (NP-C/VEGFtg NSCs) or after the cerebellum was directly injected with VEGF-loaded microspheres (NP-C/VEGF microsphere) (FIGS. 8B & 8C; n=3 per group, FIG. 8D; n=7 per group). *p<0.05. Data were expressed as the mean±SEM.

MODE FOR CARRYING OUT INVENTION

Figure 1A:
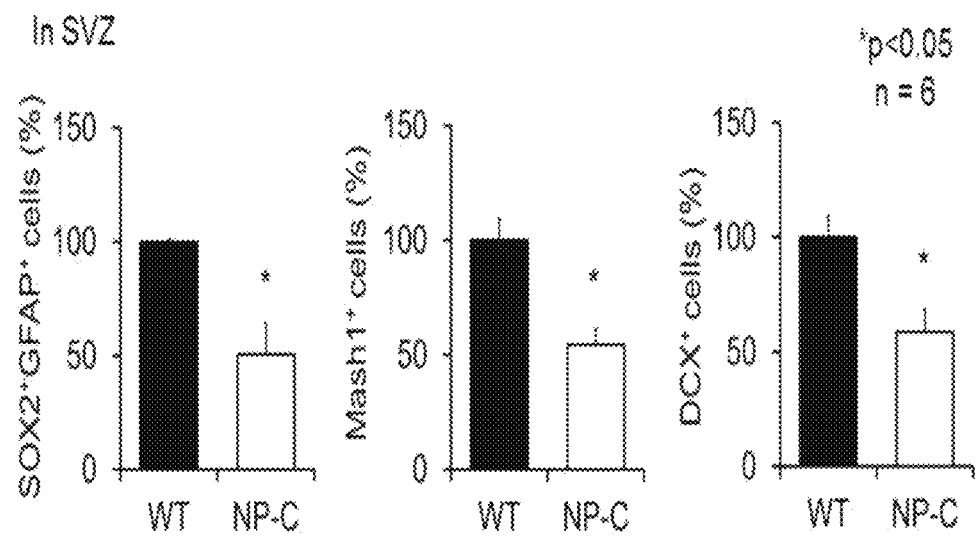
FIG. 1A confirms the proportions of neural stem cells existing in SVZ of normal (WT) and NP-C mice (n=6 per group). *$p<0.05$. Data were expressed as the mean±SEM.

Hereinafter, examples of the present invention will be described in detail.

Example 1

Materials and Methods 1-1. Preparation of Mice

A strain of NPC mutant mice deficient in Balb/C and NPC1 genes (NP-C mice: weighing less than normal mice of the same week age, showing limb jerking and seizure due to severe motor function impairment from 4-6 weeks of age, and being approximately 9-10 weeks in life-expectancy) was maintained through genotyping through PCR, and each strain of NPCf$^{fl/fl}$ and VEGFf$^{fl/fl}$ mice was maintained through strain cross. The mice were allocated to experimental groups using the block randomization method. In order to eliminate prejudice, there was no involvement in data collection and data analysis. All mice experiments were approved by the Kyungpook National University Institutional Animal Care and Use Committee (IACUC).

1-2. Injection of Medicine and Neural Cells

For injection of NPC$^{fl/fl}$ or VEGF$^{fl/fl}$ mice with normal neural stem cells, VEGF-overexpressing neural stem cells, VEGF-overexpressing vector, or GFAP/CD133 spilt-cre, the mice were anesthetize with a mixture of 100 mg/kg ketamine and 10 mg/kg xylazine. The mice were injected with normal neural stem cells (~1×10$^6$ cells/3 ul), VEGF-overexpressing neural stem cells (~1×10$^6$ cells/3 ul), VEGF-overexpressing vector (MGC 12075 clone, Thermo Scientific) (3 ul), and NPC$^{fl/fl}$ or VEGF$^{fl/fl}$ mice were daily injected with GFAP/CD133 spilt-cre (1:1.5, 2 ul for each).

In addition, 1.63 um-diameter polystyrene/divinylbenzene-coated fluorescent iron oxide particles (MPIOs, 3.00 mg Fe/ml, green fluorescent dye: 480 nm excitation, 520 nm emission; Bangs Laboratories, Fishers, Ind., USA) were used for investigating the migration of neural stem cells, and a total volume of 1.5 ul of MPIO (0.67 mg Fe/ml) mixed with 0.05 mg/ml PLL (Sigma) was injected to SVZ of each mouse. The injection rate of cells and medicines was a flow rate of 0.3 μl/min.

For the direct injection of VEGF microspheres into the cerebellum, a glass capillary (1.2 mm×0.6 mm) was used for transplantation of VEGF microspheres into the cerebellum. The injection coordinates were+5.52 mm anterior relative to the bregma and 2.50 mm in the injection depth. Regarding the injection rate, 3 mg was transplanted at a flow rate of 0.15 μl/min.

1-3. Preparation of VEGF-Containing Microspheres

For the preparation of VEGF-containing microspheres, human recombinant vascular endothelial growth factor (VEGF) was used after purchase from R&D System (Catalog No. 293-VE-010). A water-in-oil-in-water emulsification method was used to prepare poly(lactic-co-glycolic acid) (PLGA) microspheres containing the human recombinant vascular endothelial growth factor (VEGF). The human recombinant vascular endothelial growth factor-A (VEGF-A) was encapsulated in PLGA microspheres (1:1 of lactic acid and glycolic acid in PGLA and a molecular weight of 40,000-75,000).

1-4. Immunofluorescent Staining

The brain tissue of the mice was cut into a thickness of 50 um using a vibratome, and then cultured together with anti-VEGF (rabbit, 1:500, abcam), anti-SOX (mouse, 1:100, R&D), anti-GFAP (rabbit, 1:500, DAKO), anti-Iba-1 (rabbit, 1:500, DAKO), and anti-Calbindin (rabbit, 1:100, Millipore). For the investigation of the accumulation degree of cholesterol, the tissue of the mice was subjected to filipin staining. The SVZ, thalamus, cortex, and cerebellum were analyzed using a laser scanning confocal microscope equipped with Fluoview SV1000 imaging software (Olympus FV1000) or with an Olympus BX51 microscope. Metamorph software (Molecular Devices) was used to quantify the percentage of the stained part relative to the area of the whole tissue. The number of cells in the stained part was quantified by Visiomorph software (VisioMorph) using Stereology.

1-4. Culture of Neurospheres and Culture of Normal Cells and VEGF-Overexpressing Neural Stem Cells For the investigation of the abnormal migration, into the thalamus, of neural stem cells of mice with damaged SVZ or NP-C mice injected with VEGF-overexpressing neural stem cells, the SVZ and thalamus parts were extracted from the mouse brains. Each tissue was extracted in ice-cold Hibernate A/B27/Glutamax medium (HABG) (Invitrogen), and then dissociated by reaction at 37° C. for 30 minutes through immersion in papain solution (Worthington). Thereafter, the dissociated tissue was centrifuged using Optiprep (Sigma) density gradient solution, and a layer containing neural stem cells was isolated, and cultured in Neurobasal A (Invitrogen)/B27 medium containing glutamax (0.5 mM), gentamycin (10 ug/ml, Invitrogen), mouse fibroblast growth factor 2 (mFGF2, 5 ng/ml, Invitrogen), and mouse platelet-derived growth factor-bb (mPDGFbb, 5 ng/ml, Invitrogen) for one week. The cultured neural stem cells grew to spherical neurospheres, and after one week, the cells were collected and dissociated, and then cultured in 24-well plate at 1×10$^4$ cells. The neurospheres generated after 1-week culture were counted on a microscope, and the minimum cut-off size of neurospheres was limited to 50 um. For culture of neural stem cells for injection of normal and VEGF-overexpressing neural stem cells into SVZ of NP-C mice, when the neurospheres were injected after the culture by the above-described method, the cells were separated by Triple select (Gibco) solution and single cells were injected.

1-6. Lipid Measurement

The cerebrum and cerebellum of each mouse were extracted, and a homogeneous buffer containing 50 mM HEPES (Invitrogen), 150 mM sodium chloride (NaCl) aqueous solution (Sigma), 0.2% Igepal CA-630 (Sigma), and protease inhibitor (Milipore) was added, and the mixture was homogenized using a homogenizer, and centrifuged at 13,000 rpm for 10 minutes. After 10 minutes, additional centrifugation was conducted at 13,000 rpm for 30 minutes. After 30 minutes, the supernatant was taken, and dichloromethane (DCM, Sigma), DCM:M (dichloromethane:

methanol=1:3, Sigma) and 10% sodium hypochlorite (NaHCl) were sequentially added thereto, and the mixture was centrifuged at 13,000 rpm for 1 minute, and then only organic dissolution layer was separated. The separated sample was dried using a rotary vacuum evaporator. As described above, the dried lipid extract was re-suspended in 0.2% Igepal CA-630 (Sigma), and then the concentration of each lipid was measured using UPLC system.

1-7. Cholesterol Measurement

The cerebrum of each mouse was extracted, and a homogenous buffer containing 50 mM phosphate buffer, 500 mM sodium chloride (NaCl) aqueous solution, 25 mM cholic acid, and 0.5% Triron X-100 was added thereto, and the mixture was homogenized using a homogenizer, and centrifuged at 13,000 rpm for 10 minutes. After 10 minutes, only the organic dissolution layer was separated, and the cholesterol level was measured using Amplex Red Cholesterol Assay Kit (Molecular Probes).

1-8. Sensory Ability Tests

For investigation of sensory ability of mice with damaged SVZ or NP-C mice injected with VEGF-overexpressing neural stem cells, hot-plate test and tail-flick test were performed. For the hot-plate test, a heating apparatus (Panlab/Harvard Apparatus, Spain) was maintained at 50° C., and respective mice were located at the end of the heated surface, and the first nociception, that is, the time to jump or paw licking was measured. The cut-off time was 60 seconds. Between the measurements, the heated surface was washed with a detergent and ethanol, and the temperature thereof was maintained at 50° C. For the tail-flick test, the mouse was wrapped in a dark cloth, and then the tail was placed on a heated instrument surface (Panlab/Harvard Apparatus, Spain), and the time taken for the tail to respond was measured.

1-9. Motor Ability Tests (Beam Walking Test)

For investigation whether motor ability of mice with damaged SVZ or NP-C mice injected with VEGF-overexpressing neural stem cells is improved, open field, rota-rod, and beam tests were performed. The mice with the cerebellum directly injected with VEGF microspheres was subjected to rota-rod test. In the open field test, the mouse was placed in a square box for 10 minutes to measure overall activity and the time spent wandering the wall and center. For the rota-rod test (Ugo Basile, Comerio, VA, Italy), a machine equipped with a 3-cm diameter rod that was properly machined to provide grip was rotated at a rotation velocity of 4 rpm, and rota-rod exercise was conducted three times or more to measure the endurance time of a test animal in seconds, and the mean value thereof was recorded. Each rota-rod exercise test should not exceed 5 minutes in each time. In the beam test, a mouse was placed on the start point on a 6 mm or 12 mm-width rod, and then the time taken for the mouse to move to the end point was measured.

1-10. Real-Time Quantitative PCR

For investigation of expression level in SVZ neurons of NP-C mice, the SVZ of the mice was isolated, and then neuron stem cells were isolated therefrom. The expression level of VEGF in the isolated neuron stem cells was measured using real-time quantitative PCR. Total RNA was extracted from the neurons using RNeasy Plus mini kit (Qiagen, Korea, Ltd), and a kit of Clontech (Mountain View, Calif.) was used to synthesize 5 μg of cDNA from the total RNA. In addition, Corbett research RG-6000 real-time PCR instrument was used to perform real-time quantitative PCR by repeating 40 cycles each composed of 95° C. for 10 min, 95° C. for 10 sec, 58° C. for 15 sec, and 72° C. for 20 sec.

1-11. Statistical Analysis

Comparisons of respective groups were performed with Student's t-test. For comparison between another group and two or more groups, one-way analysis of variance (ANOVA) and Tukey's HSD test were performed. The comparison of the overall survival rate was performed using Log-rank test. SPSS statistical software was used for all statistical analyses. Data were considered to be significant at $p<0.05$, $p<0.01$, and $p<0.001$.

Example 2

Confirmation of Proportions of Neural Stem cells and VEGF expression levels in SVZ of NPC mice For investigation of the proportions of neural stem cells existing in SVZ of 6-week-old NP-C mice, SVZ of each of normal and NP-C mice was immunofluorescent stained by the method described in Example 1-3 above. As a result, FIG. 1A confirmed reductions of neural stem cells (SOX2+/GFAP+, Mash1+, and DCX+ cells) (*$p<0.05$. n=6 per group).

Figure 1B:
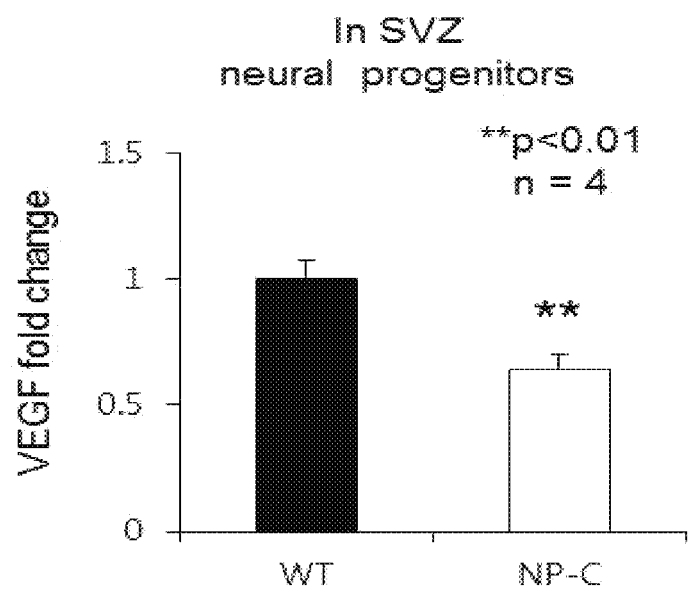
FIG. 1B confirms the expression of VEGF in neural stem cells isolated from SVZ tissue of normal (WT) and NP-C mice (n=4 per group). **$p<0.01$. Data were expressed as the mean±SEM.

For investigation of the expression level of VEGF in SVZ of 6-week-old NP-C mice, SVZ region were extracted from brains of normal mice (WT) and NP-C mice, and then neural stem cells were isolated. Total RNA was extracted from the isolated neural stem cells by the method described in Example 1-9 above, and then cDNA was synthesized, and the expression level of VEGF expressed in neurons were analyzed by real-time quantitative PCR. The results are shown in FIG. 1B (**$p<0.01$. n=4 per group).

Figure 1C:
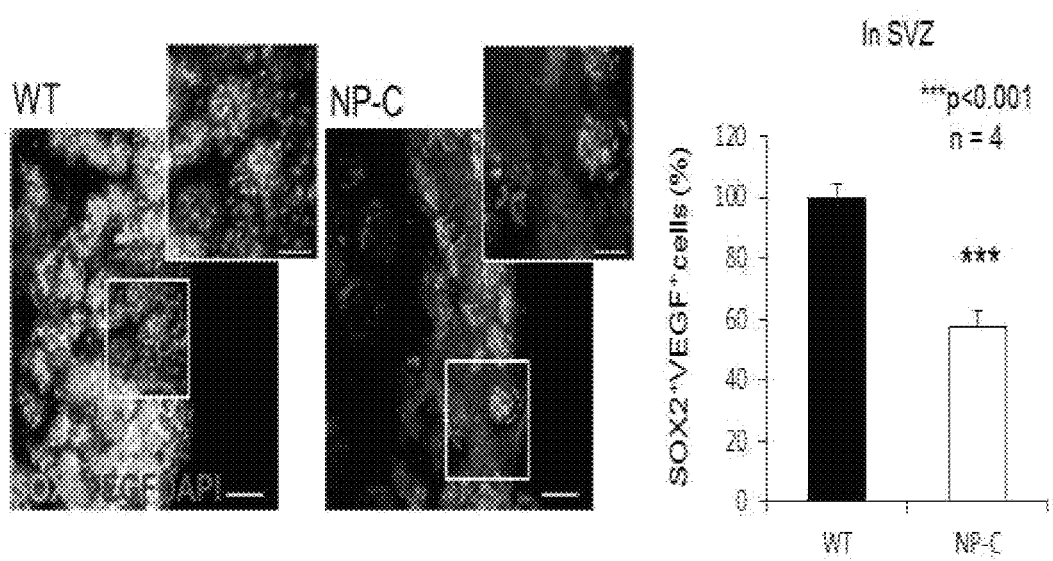
FIG. 1C confirms VEGF expressed in neural stem cells through immunofluorescent staining of normal and NP-C mouse SVZ (left) and shows a graph of quantification therefor (right) (n=4 per group). ***$p<0.001$. Data were expressed as the mean±SEM.

SVZ of each mouse was immunofluorescent stained by the method described in Example 1-3 above using neural stem cell labeling antibody and VEGF antibody. The results are shown in FIG. 1C (**$p<0.01$. n=4 per group).

As shown in FIG. 1, it could be confirmed that the survival rates of the neural stem cells existing in the SVZ environment were decreased and the expression of VEGF in neurons was reduced in NP-C mice compared with normal mice (WT).

Example 3

Confirmation of Abnormal Migration of Neural Stem Cells in SVZ Environment

It has been known that neural stem cells existing in normal SVZ environment can migrate to the olfactory bulb (OB) through the rostral migratory stream (RMS), and especially, VEGF expressed in neural stem cells is involved in such migration (See Neuron. 70, 687-702, 2011; J Neurosci. 29, 8704-8714, 2009; J Neurosci Res. 88, 248-257, 2010).

Figure 2A:
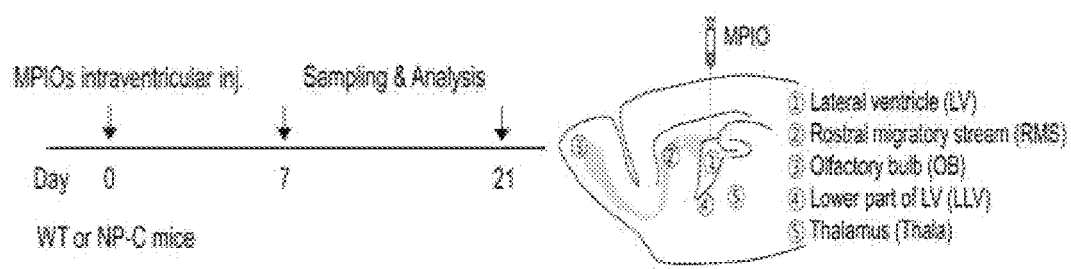
FIG. 2A shows an experimental design for investigating the migration of SVZ neural stem cells by injection of the neural stem cell labeling fluorescent substance MPIO into SVZ of normal and NP-C mice.
Figure 2B:
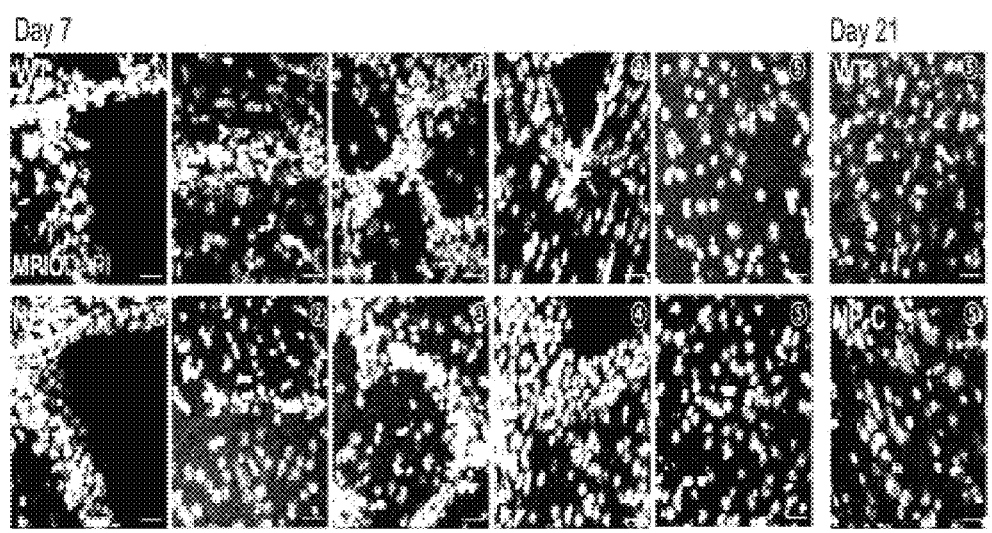
FIG. 2B confirms the presence or absence of MPIO fluorescent substance-labeled neural stem cells in different brain regions on days 7 and 21 after the injection of MPIO into normal and NP-C mouse SVZ, and shows a graph of quantification therefor (n=6 per group, ①=LV, ②=RMS, ③=OB, ④=LLV, ⑤=thalamus). *$p<0.05$, $p<0.01$, *$p<0.001$. Data were expressed as the mean±SEM.

For investigation of migration patterns of VEGF expression-reduced neural stem cells in SVZ of NP-C mice, the neural stem cell labeling fluorescent substance MPIO was injected into SVZ of normal and NP-C mice (FIG. 2A). It was confirmed that after 7 days, the MPIO labeled neural stem cells of normal mice existed a lot in RMS and OB, whereas the neural stem cells of NP-C mice existed a lot in the thalamus, and after 21 days, the neural stem cells of NP-C mice existed a lot in the thalamus (FIG. 2B, *$p<0.05$, $p<0.01$, *$p<0.001$. n=6 per group).

That is, it could be confirmed that in the normal state, the neural stem cells in SVZ migrate a lot to RMS and OB but rarely migrate to the thalamus, whereas the VEFG expression-reduced neural stem cells do not migrate a lot and abnormally migrate to the thalamus.

Example 4

Figure 3A:
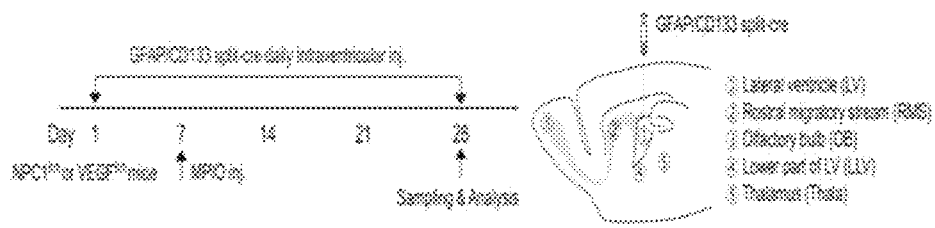
FIG. 3A shows an experimental design for investigating the effects of SVZ damage on the entire brain when, for the induction of the damage to neural stem cells existing in the SVZ environment, GFAP/CD133 split-cre was injected into SVZ of NPCf$^{fl/fl}$ or VEGFf$^{fl/fl}$ mice to reduce the expression of NPC or VEGF specifically to neural stem cells.

Effect of SVZ Environment Damage on Inflammation Responses and Cholesterol and Lipid Accumulation of the Entire Brain For investigation of the effect of the damage of neural stem cells existing in SVZ environment on the inflammation responses of the entire brain, a cannula was inserted in SVZ of 4-week-old NPCf$^{fl/fl}$ or VEGF$^{fl/fl}$ mice, and as shown in FIG. 3A, GFAP/CD133 split-cre was daily injected into SVZ for a total of 4 weeks. That is, pathological changes shown after (i) GFAP/CD133 split-cre was injected into SVZ of NPCf$^{fl/fl}$ mice to inhibit the expression of NPC1 in neural stem cells existing in SVZ, or (ii) GFAP/CD133 split-cre was injected into SVZ of VEGFf$^{fl/fl}$ mice to inhibit the expression of VEGF in neural stem cells existing in SVZ were observed.

Figure 3B:
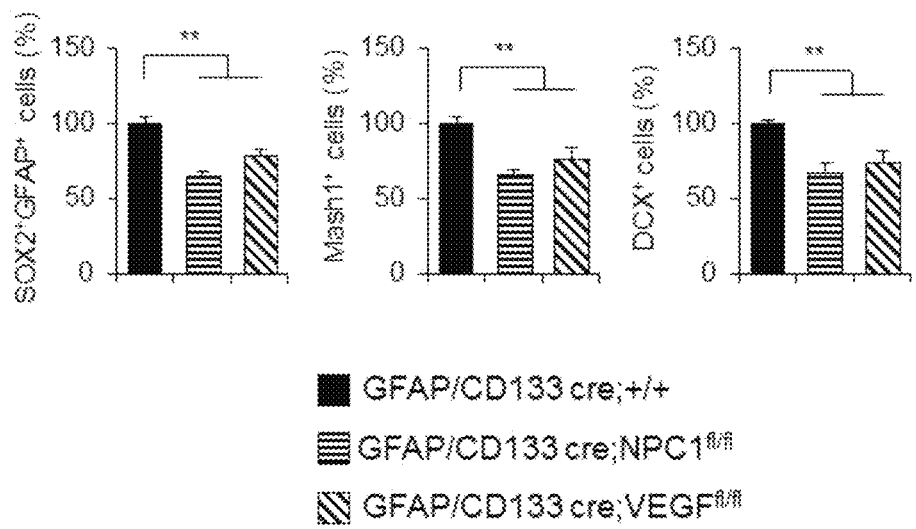
FIG. 3B confirms the proportions of neural stem cells in SVZ of NPC$^{fl/fl}$ or VEGF$^{fl/fl}$ when SVZ was injected with GFAP/CD133 split-cre for four weeks (n=6 per group). **$p<0.01$. Data were expressed as the mean±SEM.
Figure 3C:
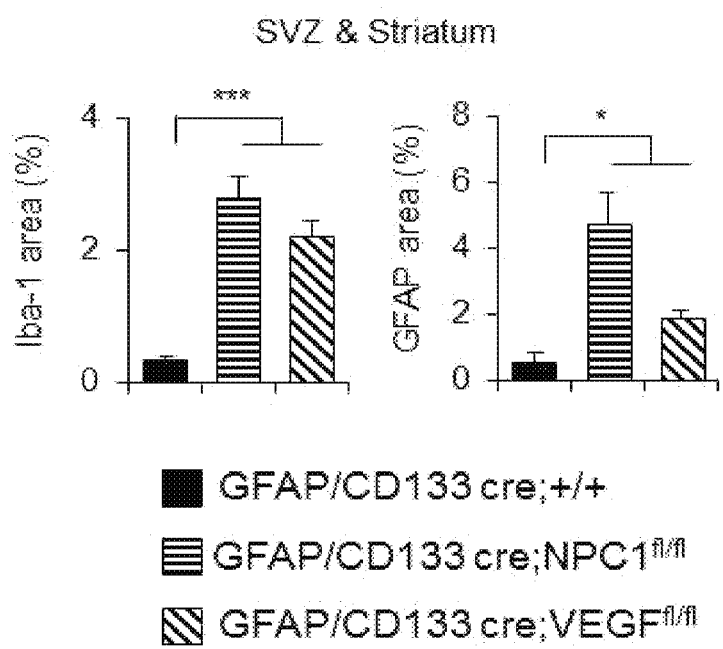
FIG. 3C confirms the inflammation responses of the SVZ environment of the NPC$^{fl/fl}$ or VEGF$^{fl/fl}$ mice when SVZ was injected with GFAP/CD133 split-cre for four weeks (GFAP: astrocyte, Iba-1: microglia. n=6 per group). *$p<0.05$, ***$p<0.001$. Data were expressed as the mean±SEM.
Figure 3D:
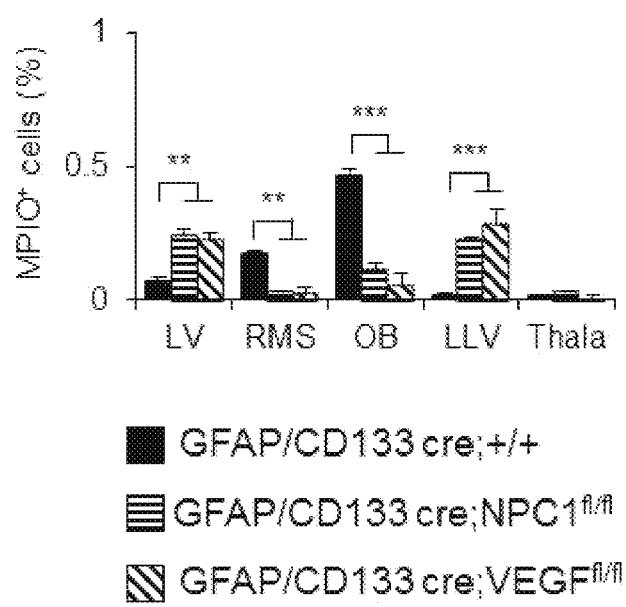
FIG. 3D confirms the presence or absence of MPIO fluorescent substance-labeled neural stem cells in different brain regions in NPC$^{fl/fl}$ or VEGF$^{fl/fl}$ mice when SVZ was injected with GFAP/CD133 split-cre and MPIO (n=6 per group). $p<0.01$, *$p<0.001$. Data were expressed as the mean±SEM.
Figure 3E:
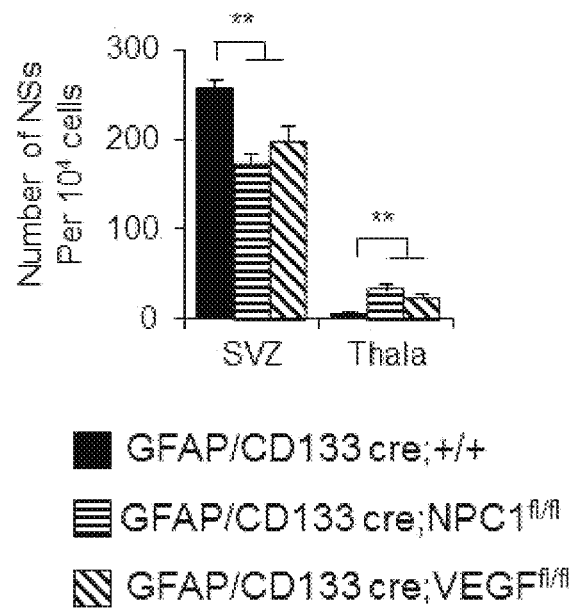
FIG. 3E confirms, through neurosphere (NS) cultures, the presence or absence of neural stem cells in SVZ and thalamus tissues of NPCf$^{fl/fl}$ or VEGF$^{fl/fl}$ mice when SVZ was injected with GFAP/CD133 split-cre for four weeks (n=6 per group). **$p<0.01$. Data were expressed as the mean±SEM.

As a result, as shown in FIGS. 3B and 3C, it was confirmed that the survival rates of neural stem cells existing in the SVZ environment of the NPC1 or VEGF expression-inhibited mice were decreased and the inflammation responses were significantly increased (GFAP: astrocyte, Iba-1: microglia. *$p<0.05$, *$p<0.001$, n=6 per group), The NPC or VEGF expression-reduced neural stem cells caused by such problems of SVZ showed abnormal migration to the thalamus (FIGS. 3D and 3E, $p<0.01$, ***$p<0.001$, n=6 per group).

Figure 3F:
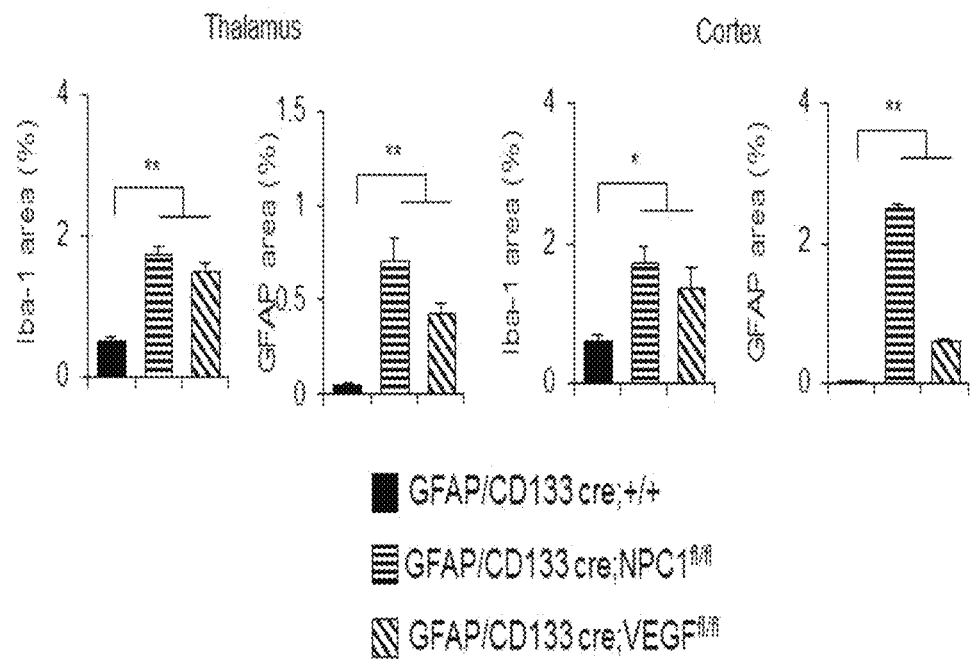
FIG. 3F confirms the inflammation responses in the thalamus and cortex of NPCf$^{fl/fl}$ or VEGF$^{fl/fl}$ when SVZ was injected with GFAP/CD133 split-cre for 4 weeks (GFAP: astrocyte, Iba-1: microglia. n=6 per group). *$p<0.05$, **$p<0.01$. Data were expressed as the mean±SEM.
Figure 3G:
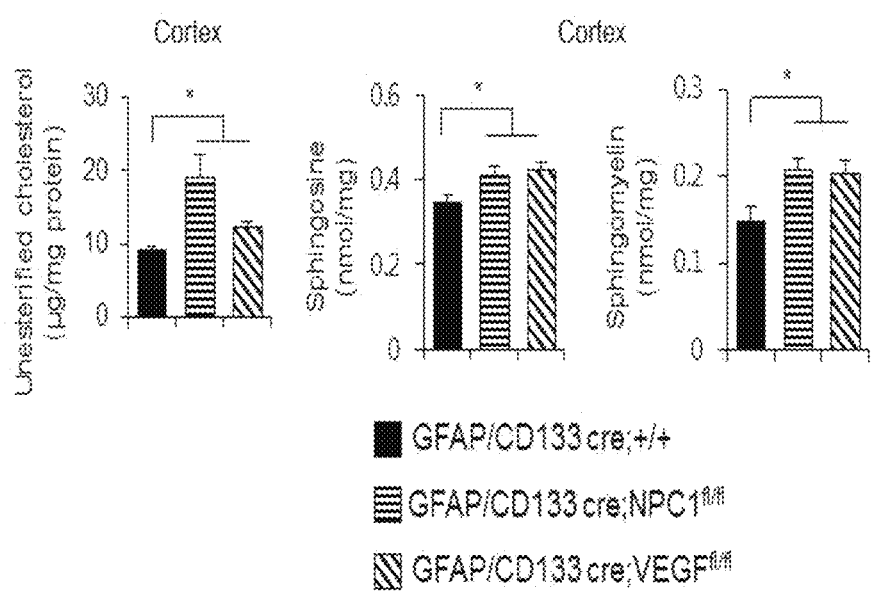
FIG. 3G confirms the cholesterol and lipid accumulation in the cortex of NPCf$^{fl/fl}$ or VEGFf$^{fl/fl}$ when SVZ was injected with GFAP/CD133 split-cre for 4 weeks (n=6 per group). $p<0.05$. Data were expressed as the mean±SEM.

It was confirmed that the abnormal migration of NPC or VEGF expression-reduced neural stem cells to the thalamus also increased the inflammation responses in the thalamus and cortex (FIG. 3E), and also increased the cholesterol and lipid accumulation, which is a major pathological pattern in NP-C mice (FIGS. 3F and 3G, GFAP: Iba-1: microglia. *$p<0.05$, **$p<0.01$. n=6 per group).

It could be seen from the results above that the damage to SVZ environment reduces the survival rates of neural stem cells existing in SVZ environment and causes abnormal migration of NPC or VEGF expression-reduced neural stem cells to the thalamus, thereby increasing the inflammation responses in the thalamus and, furthermore, inducing the inflammation responses and the cholesterol and lipid accumulation in the cortex. This indicates that the damage to SVZ environment can affect the entire brain.

Example 5

Effects of SVZ Environment Damage on Sensory and Motor Abilities

For investigation whether inflammation responses and cholesterol and lipid accumulation in the entire brain due to SVZ environment damage affect sensory and motor abilities, NPC$^{fl/fl}$ or VEGF$^{fl/fl}$ mice with SVZ injected with GFAP/CD133 split-cre for a total of 4 weeks were subjected to hot-plate and tail-flick tests as sensory ability test, and open field, rota-rod, and beam tests as motor ability tests.

Figure 4A:
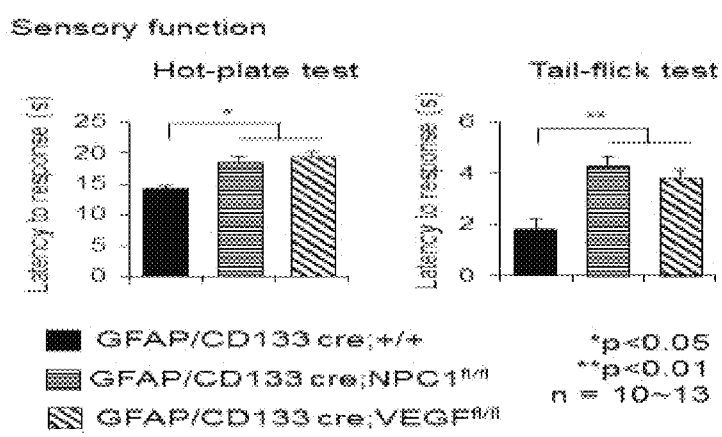
FIGS. 4A and 4B confirm the presence or absence of the impairments of sensory function (FIG. 4A) and motor function (FIG. 4B) of NPC$^{fl/fl}$ or VEGF$^{fl/fl}$ with SVZ injected with GFAP/CD133 split-cre for 4 weeks (n=10-13 per group). *$p<0.05$, **$p<0.01$. Data were expressed as the mean±SEM.
Figure 4B:
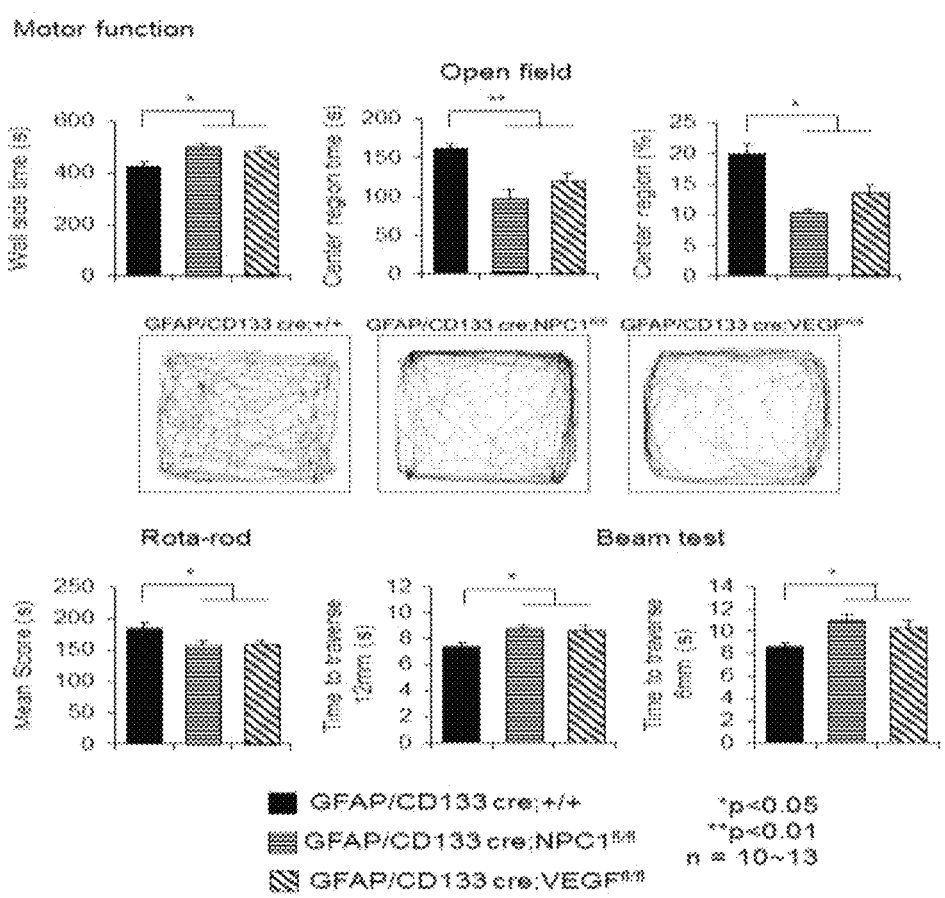

As a result, the mice with damaged SVZ environment showed reduced sensory and motor abilities (FIGS. 4A and 4B, *$p<0.05$, **$p<0.01$. n=10-13 per group).

It could be seen from the above results that the inflammation responses and the cholesterol and lipid accumulation in the entire brain due to SVZ environment damage reduce sensory and motor abilities.

Example 6

Figure 5A:
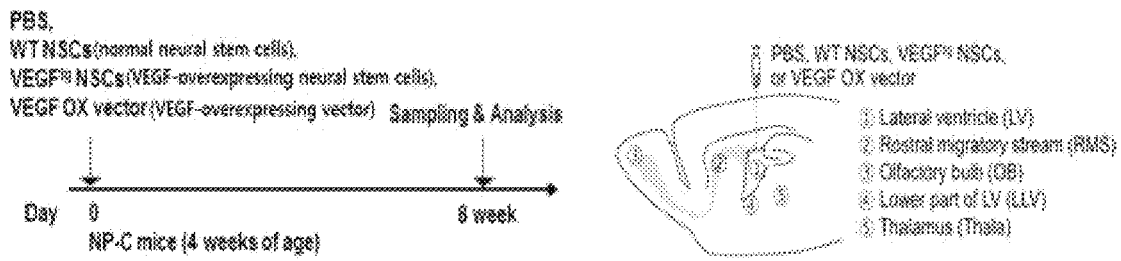
FIG. 5A shows an experimental design for injection of normal neural stem cells (WT NSCs), VEGF-overexpressing neural stem cells (VEGFtg NSCs), and VEGF-overexpressing vector (VEGF OX vector) in order to improve the damaged SVZ environment of NP-C mice.

Mitigation of Inflammation Responses Through Improvement of Damaged SVZ Environment of NP-C Mice In cases of NP-C mice, the expression of VEGF has been reduced in neural stem cells existing in SVZ, and therefore, it was investigated whether the inflammation responses in the entire brain can be mitigated through VEGF increase in the damaged SVZ environment. Specifically, as shown in FIG. 5A, SVZ of NP-C mice was injected with normal neural stem cells, VEGF-overexpressing neural stem cells, and VEGF-overexpressing vector twice a week for a total of 4 weeks.

Figure 5B:
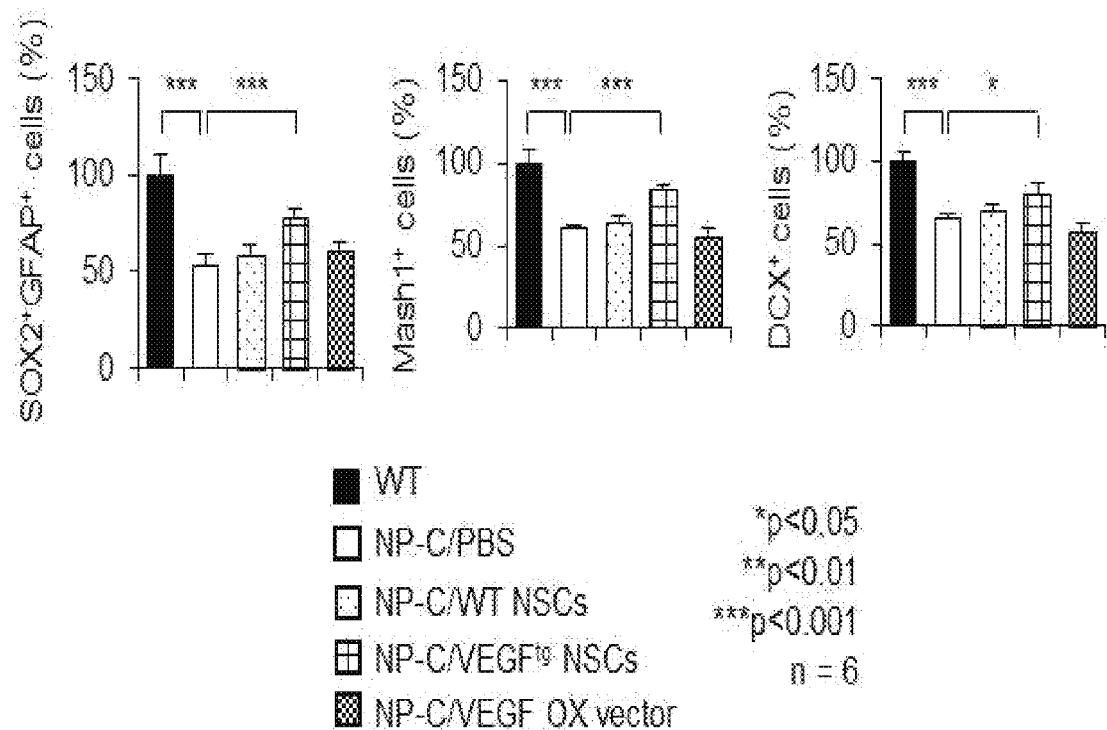
FIG. 5B confirms the percentages of neural stem cells in SVZ after NP-C mice were injected with normal neural stem cells, VEGF-overexpressing neural stem cells, and VEGF-overexpressing vector twice a week for a total of 4 weeks (n=6 per group). *$p<0.05$, ***$p<0.001$. Data were expressed as the mean±SEM.

It was confirmed from the results in FIG. 5B that the reduced survival rates of neural stem cells were increased only when VEGF-overexpressing neural stem cells were injected into SVZ of NP-C mice (*$p<0.05$, ***$p<0.001$. n=6 per group).

Figure 5C:
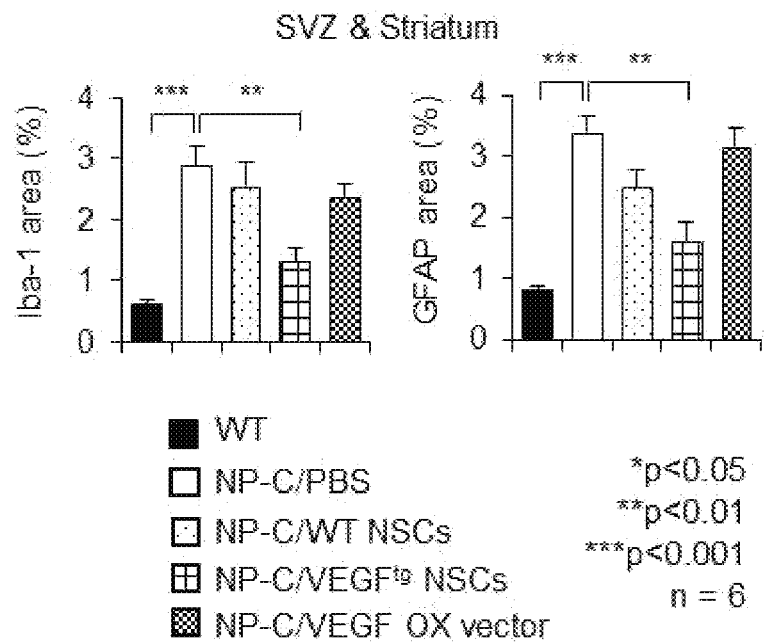
FIGS. 5C and 5D confirm the inflammation responses in the SVZ, thalamus, and cortex after SVZ of NP-C mice was injected with normal neural stem cells, VEGF-overexpressing neural stem cells, and VEGF-overexpressing vector twice a week for a total of 4 weeks (GFAP: astrocyte, Iba-1: microglia. n=6 per group). $p<0.01$, *$p<0.001$. Data were expressed as the mean±SEM.
Figure 5D:
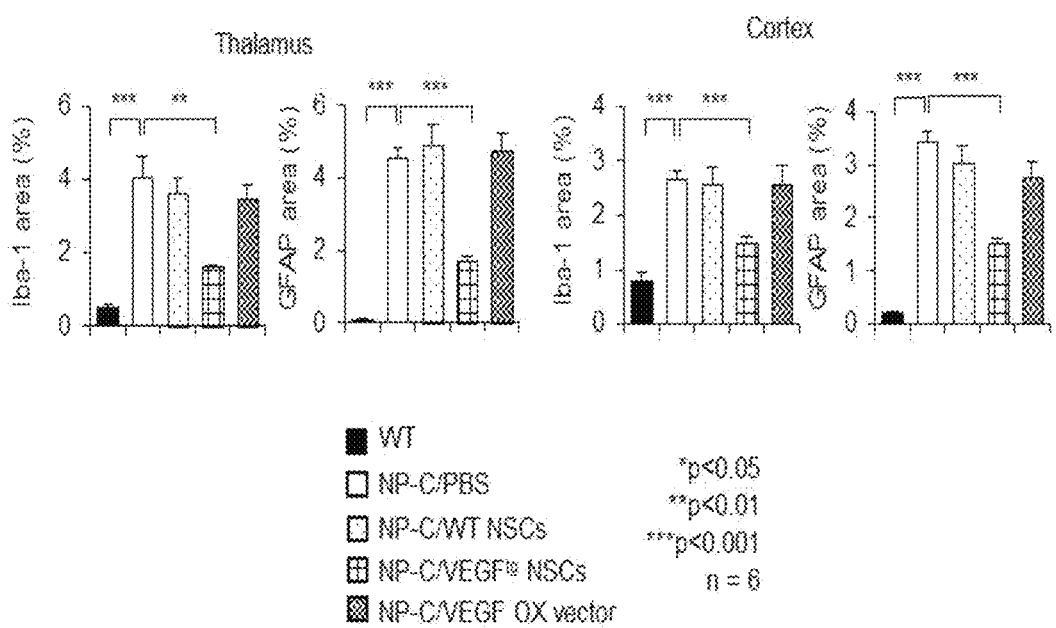

It was confirmed from the results in FIGS. 5C and 5D that the SVZ environment and the inflammation responses in the thalamus and cortex of NP-C mice were reduced only when VEGF-overexpressing neural stem cells were injected (GFAP: astrocyte, Iba-1: microglia. **n=6 per group). It can be seen from the above results that the injection of normal neural stem cells is insufficient to increase the reduced VEGF in SVZ of NP-C mice, and VEGF-overexpressing vector is also insufficient to mitigate the inflammation responses since the vector cannot increase VEGF specifically to neural stem cells.

Figure 5E:
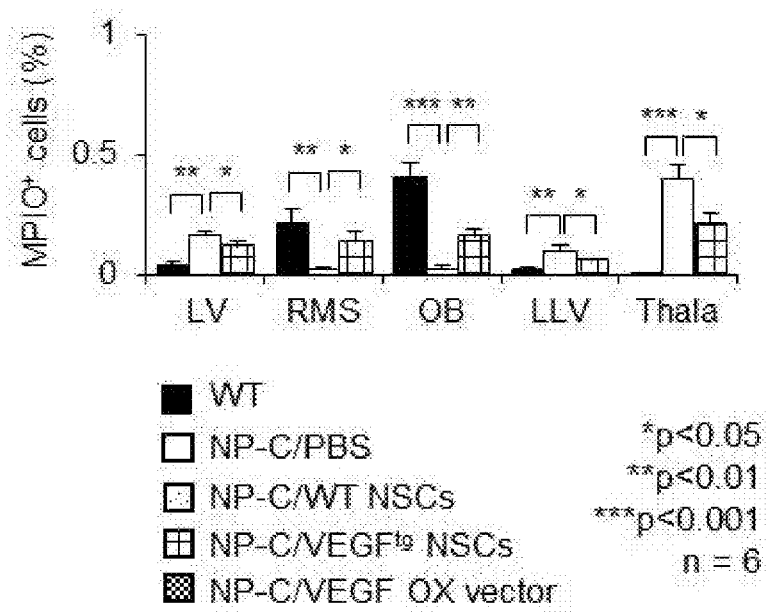
FIG. 5E confirms the existence proportions (%) of MPIO fluorescent substance-labeled neural stem cells in different brain regions in NP-C mice with SVZ injected with VEGF-overexpressing neural stem cells twice a week for a total of four weeks (n=6 per group). *$p<0.05$, $p<0.01$, *$p<0.001$. Data were expressed as the mean±SEM.
Figure 5F:
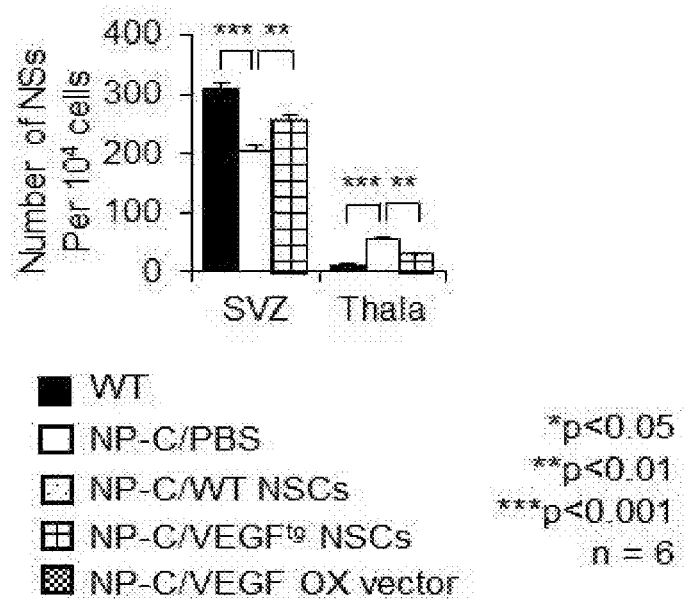
FIG. 5F confirms, through neurosphere (NS) cultures, the presence or absence of neural stem cells in SVZ and thalamus tissues of NP-C mice with SVZ injected with VEGF-overexpressing neural stem cells twice a week for a total of four weeks (n=6 per group). $p<0.01$, *$p<0.001$. Data were expressed as the mean±SEM.

Furthermore, the VEGF-overexpressing neural stem cells mitigated the abnormal migration of neural stem cells in SVZ of NP-C mice to the thalamus (FIGS. 5E and 5F, ***n=6 per group).

It can be therefore seen that when VEGF-overexpressing neural stem cells capable of sufficiently restoring reduced VEGF were injected into SVZ in order to improve the SVZ environment of NP-C mice, the abnormal migration of neural stem cells can be reduced and the inflammation responses in the entire brain can be mitigated.

Example 7

Reduction of Cholesterol Accumulation Through Improvement of Damaged SVZ Environment of NP-C Mice For investigation whether the improvement of SVZ environment by the injection of VEGF-overexpressing neural stem cells into NP-C mice can reduce cholesterol and lipid accumulation, which is a major pathological pattern of NP-C mice, the cortex region of NP-C mice, which was injected with normal neural stem cells, VEGF-overexpressing neural stem cells, and VEGF-overexpressing vector was subjected filipin staining to investigate the cholesterol accumulation levels.

Figure 6A:
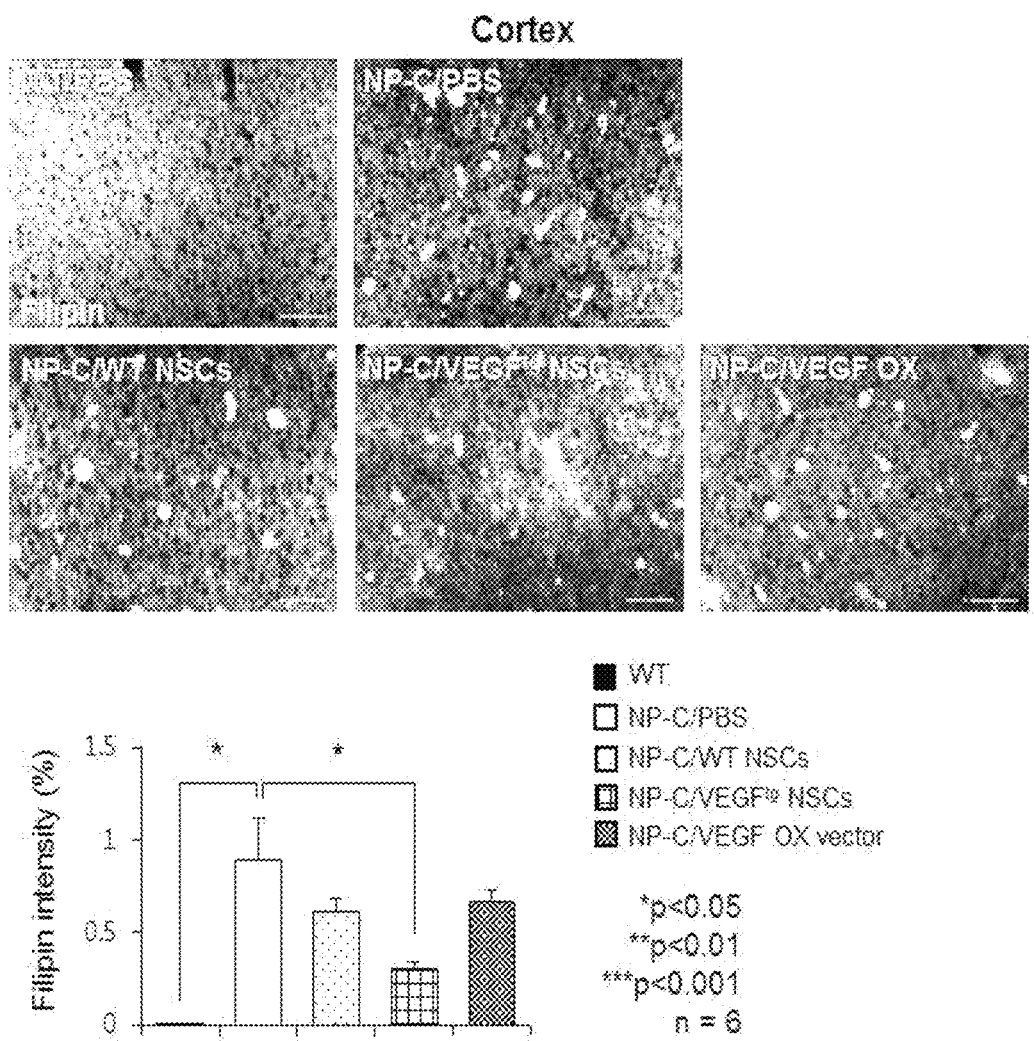
FIG. 6A confirms, through filipin immunostaining, the cholesterol levels accumulated in the cerebrum after SVZ of NP-C mice was injected with normal neural stem cells, VEGF-overexpressing neural stem cells, and VEGF-overexpressing vector twice a week for a total of 4 weeks, and shows a graph of quantification therefor (n=6 per group). $p<0.05$. Data were expressed as the mean±SEM.
Figure 6B:
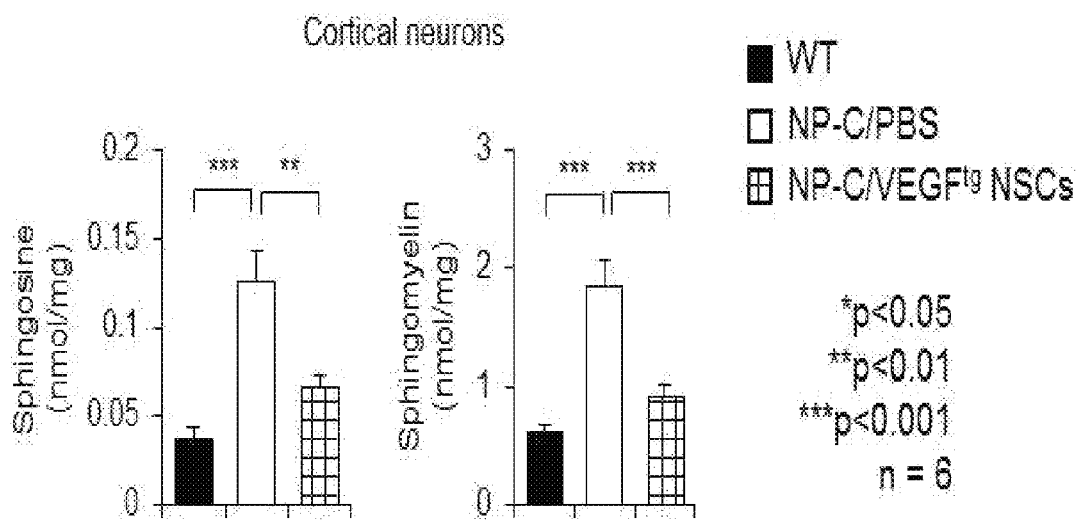
FIG. 6B confirms the lipid levels accumulated in the cerebrum after SVZ of NPC mice was injected with VEGF-overexpressing neural stem cells twice a week for a total of 4 weeks (n=6 per group). $p<0.01$, *$p<0.001$. Data were expressed as the mean±SEM.

As shown in FIGS. 6A and 6B, it was confirmed that the cholesterol accumulated in the cortex of NP-C mice with the SVZ environment injected with VEGF-overexpressing neural stem cells were reduced, and the lipid accumulation was also reduced (*$p<0.05$, $p<0.01$, *$p<0.001$, n=6 per group).

It can be seen from the above results that the improvement of SVZ environment by the injection of VEGF-overexpressing neural stem cells can reduce the cholesterol and lipid accumulation in the entire brain.

Example 8

Improvement of Sensory and Motor Abilities Through Improvement of Damaged SVZ Environment of NP-C Mice It was investigated whether the improvement of SVZ environment by the injection of VEGF-overexpressing neural stem cells into NP-C mice can improve the reduced sensory and motor abilities of NP-C mice.

Figure 7A:
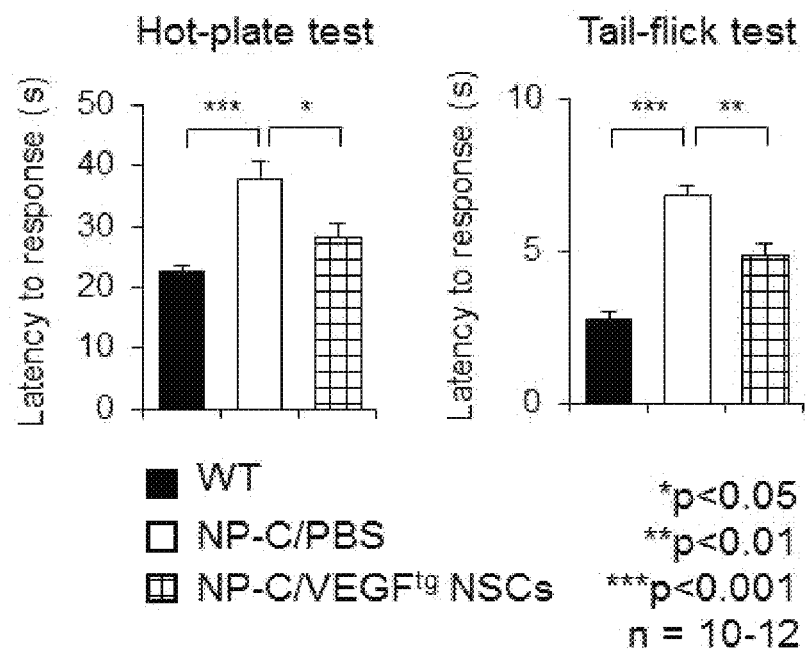
FIGS. 7A, 7B, and 7C confirm the presence or absence of the improvement of sensory function (FIG. 7A) and motor function (FIG. 7B) and the increase or decrease in survival rate (FIG. 7C) after SVZ of NP-C mice was injected with VEGF-overexpressing neural stem cells twice a week for a total of 4 weeks (n=10-12 per group). *$p<0.05$, $p<0.01$, *$p<0.001$. Data were expressed as the mean±SEM.
Figure 7B:
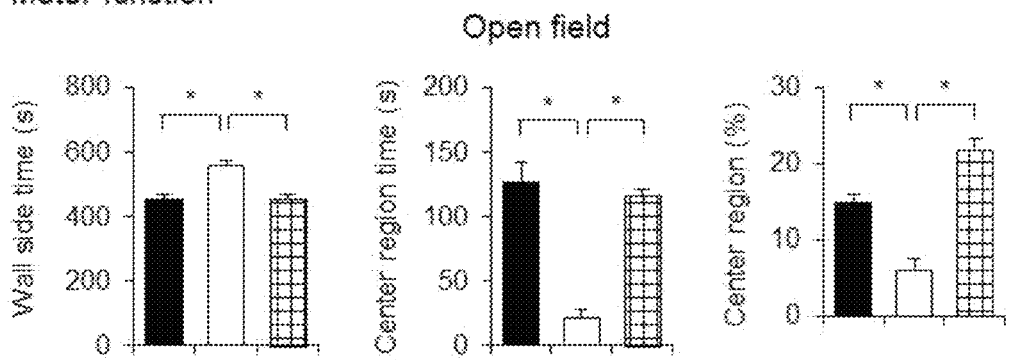
Figure 7B:
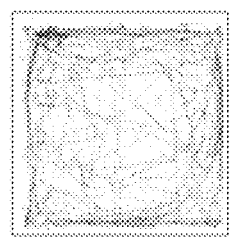
Figure 7B:
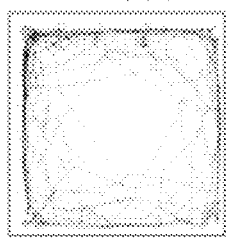
Figure 7B:
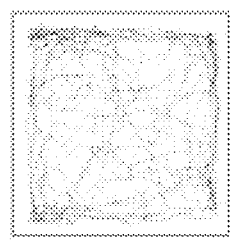
Figure 7B:
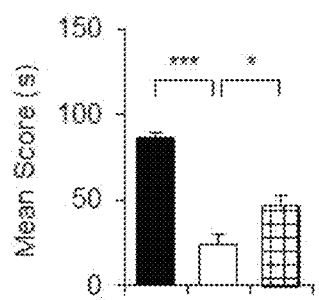
Figure 7B:
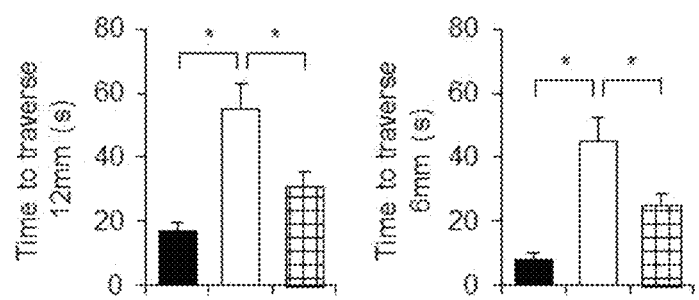
Figure 7C:
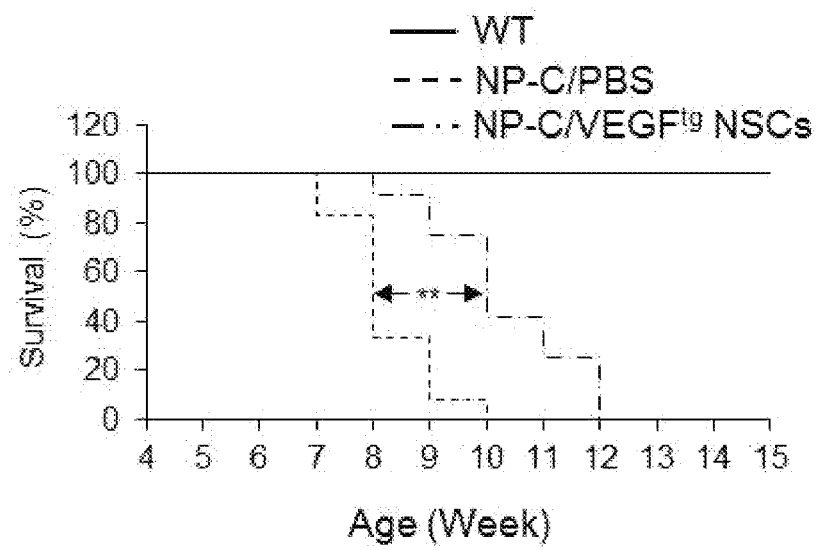

Through hot-plate and tail-flick tests as sensory ability test, and open field, rota-rod, and beam tests as motor ability tests, shown in FIGS. 7A and 7B, it can be seen that the sensory and motor abilities of NP-C mice with SVZ environment injected with VEGF-overexpressing neural stem cells were improved (*$p<0.05$. $p<0.01$, *$p<0.001$, n=10-12 per group). Furthermore, it was confirmed that the survival rate of NP-C mice was increased (FIG. 7C **$p<0.01$, n=10-12 per group).

It can be seen from the above results that the improvement of SVZ environment by the injection of VEGF-overexpressing neural stem cells can reduce the cholesterol and lipid accumulation in the entire brain, thereby improving sensory and motor abilities and increasing the survival rate.

It can be therefore seen from the above results that the improvement of SVZ environment can affect the entire brain; especially regarding the reduced VEGF in SVZ in NP-C mice, the SVZ environment can be improved only when VEGF is increased specifically to neural stem cells; and such the improvement of SVZ environment can improve the inflammation responses, cholesterol and lipid accumulation, and sensory and motor abilities in the entire brain.

Example 9

Improvement of Cerebellar Environment Through Improvement of Damaged SVZ Environment of NP-C Mice It was investigated whether the improvement of SVZ environment by the injection of VEGF-overexpressing neural stem cells into NP-C mice can also improve the cerebellar environment of NP-C mice. In addition, the improvement effects of cerebellar environment by such SVZ correction was compared with effects of direct transplant of VEGF microspheres into the cerebellum.

Figure 8A:
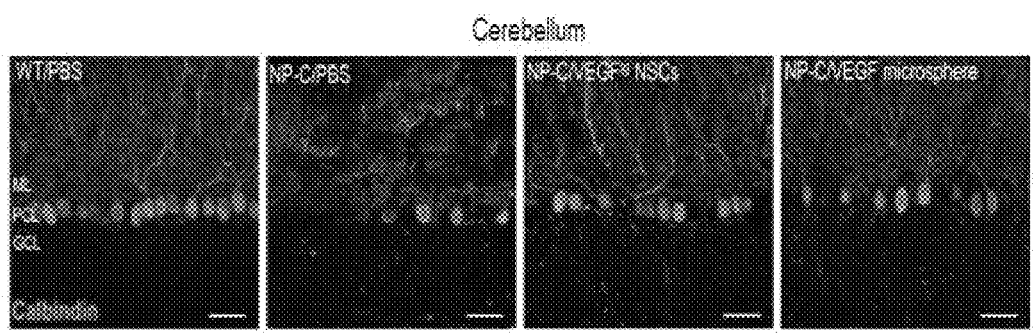
FIG. 8A confirms the decrease of neurons existing in the Purkinje cell layer (PCL) by staining the cerebellar tissues composed of molecular layer (ML), PCL, and granular cell layer (GCL) after SVZ of NP-C mice was injected with VEGF-overexpressing neural stem cells (NP-C/VEGFtg NSCs) or after the cerebellum was directly injected with VEGF-loaded microspheres (NP-C/VEGF microsphere) (left), and shows a graph of the quantification of the reduction of neurons in each of cerebellar lobe Nos. III to VIII (right) (n=3 per group). *p<0.05. Data were expressed as the mean±SEM.
Figure 8A:
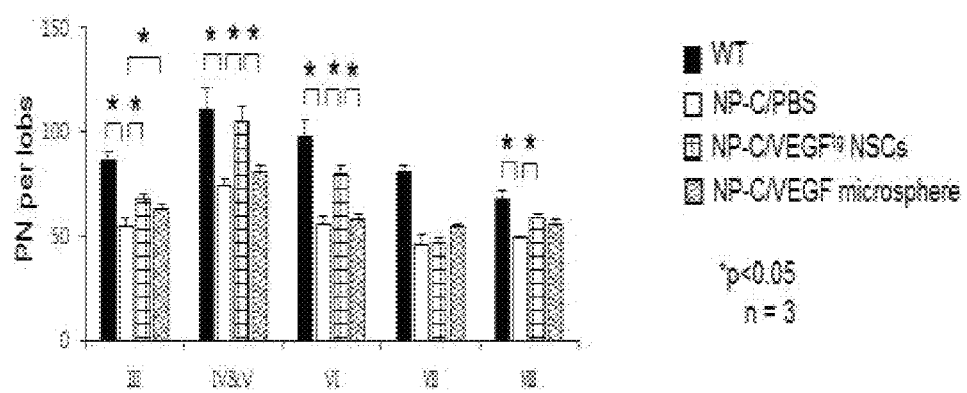
Figure 8B:
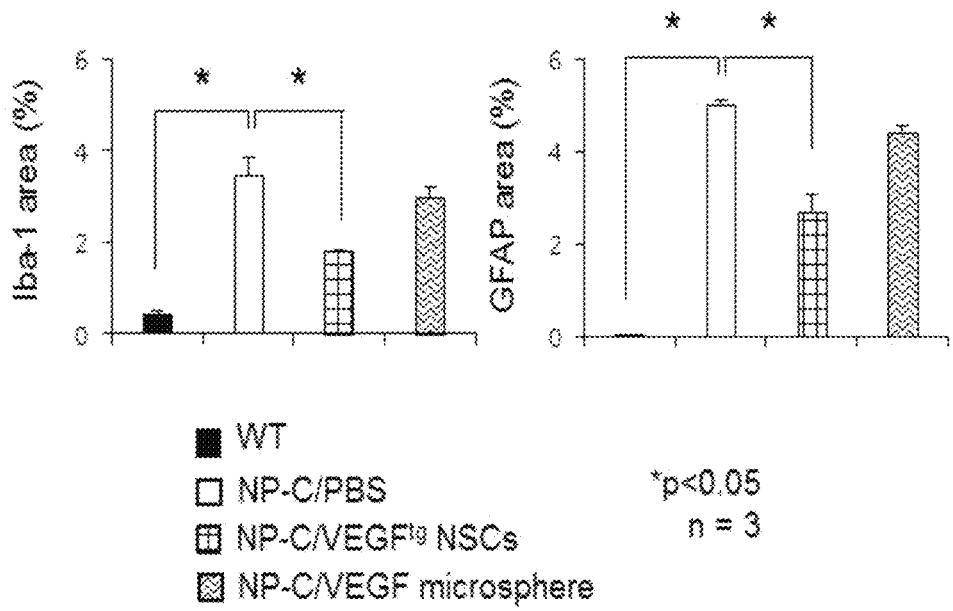
Figure 8C:
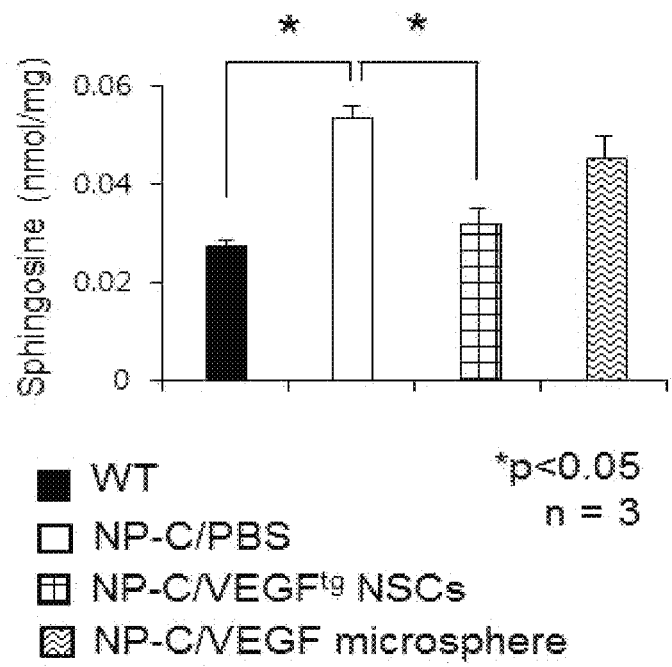

It was confirmed from FIG. 8A that Purkinje neurons (PNs) reduction was mitigated in NP-C mice with SVZ environment injected with VEGF-overexpressing neural stem cells. Such the injection of VEGF-overexpressing neural stem cells showed an excellent mitigation effect in more regions of the cerebellum than the direct transplant injection of VEGF microspheres into the cerebellum. As shown in FIG. 8B, the cerebellar inflammation responses were reduced more effectively in NP-C mice injected with VEGF-overexpressing neural stem cells, and as shown in FIG. 8C, there was also a more excellent effect in the reduction of cerebellar lipid accumulation (*$p<0.05$. n=3 per group).

As shown in FIG. 8D, the SVZ correction by the injection of VEGF-overexpressing neural stem cells improved the motor function more effectively than the direct transplant of VEGF microspheres (*$p<0.05$. n=7 per group).

Therefore, the increase of VEGF specific to neural stem cells in SVZ of NP-C mice can also improve the cerebellar environment through the improvement of SVZ environment, and this indicates that the improvement of SVZ environment is important in alleviating the pathogenesis of NP-C mice. It could be especially confirmed that the improvement of SVZ environment can alleviate pathogenesis more effectively than the direct increase of cerebellar VEGF.

What is claimed is:

1. A method for treating a neurodegenerative disease in a subject in need thereof, the method comprising administering an effective amount of a composition comprising stem cells overexpressing vascular endothelial growth factor (VEGF) as an active ingredient to a subventricular zone (SVZ) of the subject, wherein the neurodegenerative disease is selected from the group consisting of Niemann-Pick disease, Gaucher disease, Fabry disease, Tay-Sachs disease, and Sandhoff disease.

2. The method of claim 1, wherein the stem cells are at least any one selected from the group consisting of adult stem cells, embryonic stem cells, mesenchymal stem cells, tumor stem cells, and induced pluripotent stem cells.

3. The method of claim 2, wherein the adult stem cells are neural stem cells or neural progenitor cells.

4. The method of claim 1, wherein the stem cells overexpressing the vascular endothelial growth factor (VEGF) reduce a cerebral inflammation and inhibit cholesterol or sphingolipid accumulation.

5. The method of claim 1, wherein the composition is a pharmaceutical composition.

* * * * *